US010278976B2

(12) United States Patent
Weidhaas

(10) Patent No.: US 10,278,976 B2
(45) Date of Patent: May 7, 2019

(54) METHODS FOR TREATING OR PREVENTING CANCER IN A KRAS-VARIANT PATIENT AND FOR DIAGNOSING RISK OF DEVELOPING MULTIPLE PRIMARY BREAST TUMORS

(71) Applicant: Mira Dx, Inc., Los Angeles, CA (US)

(72) Inventor: Joanne Weidhaas, Los Angeles, CA (US)

(73) Assignee: Mira Dx, Inc., Los Angeles, CA (US)

(*) Notice: Subject to any disclaimer, the term of this patent is extended or adjusted under 35 U.S.C. 154(b) by 0 days.

(21) Appl. No.: 15/535,248

(22) PCT Filed: Dec. 11, 2015

(86) PCT No.: PCT/US2015/065363
§ 371 (c)(1),
(2) Date: Jun. 12, 2017

(87) PCT Pub. No.: WO2016/094854
PCT Pub. Date: Jun. 16, 2016

(65) Prior Publication Data

US 2017/0360803 A1 Dec. 21, 2017

Related U.S. Application Data

(60) Provisional application No. 62/091,357, filed on Dec. 12, 2014.

(51) Int. Cl.

| | |
|---|---|
| ***A61K 31/565*** | (2006.01) |
| ***A61K 31/138*** | (2006.01) |
| ***A61K 31/085*** | (2006.01) |
| ***A61K 31/135*** | (2006.01) |
| ***A61K 31/40*** | (2006.01) |
| ***A61K 31/4535*** | (2006.01) |
| ***A61K 31/4025*** | (2006.01) |
| ***A61K 31/4196*** | (2006.01) |
| ***A61K 31/55*** | (2006.01) |
| ***C12Q 1/6886*** | (2018.01) |

(52) U.S. Cl.
CPC .......... *A61K 31/565* (2013.01); *A61K 31/085* (2013.01); *A61K 31/135* (2013.01); *A61K 31/138* (2013.01); *A61K 31/40* (2013.01); *A61K 31/4025* (2013.01); *A61K 31/4196* (2013.01); *A61K 31/4535* (2013.01); *A61K 31/55* (2013.01); *C12Q 1/6886* (2013.01); *C12Q 2600/118* (2013.01); *C12Q 2600/156* (2013.01); *C12Q 2600/178* (2013.01)

(58) Field of Classification Search
CPC .................................................... A61K 31/565
See application file for complete search history.

(56) References Cited

U.S. PATENT DOCUMENTS

| | | | |
|---|---|---|---|
| 7,799,782 B2 * | 9/2010 | Munson ............... | C07D 231/56 514/234.5 |
| 2005/0031695 A1 | 2/2005 | Rouanet et al. | |
| 2006/0253263 A1 | 11/2006 | Meshkin | |
| 2007/0122843 A1 * | 5/2007 | Sarkar ................. | A61K 47/481 435/7.1 |
| 2010/0021529 A1 | 1/2010 | Schafer et al. | |
| 2012/0028254 A1 | 2/2012 | Weidhaas | |
| 2014/0024590 A1 | 1/2014 | Weidhaas et al. | |

FOREIGN PATENT DOCUMENTS

| | | |
|---|---|---|
| WO | WO-2008151004 A1 | 12/2008 |
| WO | WO-2012129352 A1 | 9/2012 |
| WO | WO-2014193937 A1 | 12/2014 |

OTHER PUBLICATIONS

Baldelli et al. , Oncotarget, 2015, 6(32):32368-79.*
Pilarski et al. Plos One, 2012, 7(5): e37891.*
Lu et al., Cancer Research, 1010, 70(16): 6509-15.*
Elena et al., Cancer Research, 2008, 68(20): 8535-40.*
Carney et al., and Maturitas, 2006, 53(1): 65-76.*
Alkner et al., "Tamoxifen reduces the risk of contralateral breast cancer in premenopausal women: Results from a controlled randomised trial," European Journal of Cancer, (2009), vol. 45, No. 14, pp. 2496-2502.
Amer, "Multiple neoplasms, single primaries, and patient survival," Cancer Management and Research, (2014), vol. 6, pp. 119-134.
Anderson et al., "Reproductive risk factors and breast cancer subtypes: a review of the literature," Breast Cancer Res Treat (2014), vol. 144, No. 1, pp. 1-10.
Anderson et al., "Effects of Conjugated Equine Estrogen in Postmenopausal Women with Hysterectomy," JAMA, (2004), vol. 291, No. 14, pp. 1701-1712.
Beral, "Breast cancer and hormone-replacement therapy in the Million Women Study," Lancet (2003) vol. 362, pp. 419-427.
Bhatia, "Genetic Variation as a Modifier of Association Between Therapeutic Exposure and Subsequent Malignant Neoplasms in Cancer Survivors," Cancer (2015), vol. 121, No. 5, pp. 648-663, (first published Oct. 29, 2014).

(Continued)

*Primary Examiner* — Rei Tsang Shiao
(74) *Attorney, Agent, or Firm* — Goodwin Procter LLP

(57) ABSTRACT

The invention relates to methods for preventing cancer in a KRAS-variant subject which include administering to the KRAS-variant subject an amount of estrogen effective to reduce the risk of developing cancer. In another aspect, the invention further relates to methods for treating cancer in a KRAS-variant subject, which include gradually decreasing estrogen exposure in the KRAS-variant subject to reduce the risk of aggressive tumor growth. In another aspect, the invention relates to a method of predicting an increased risk of developing a second, independent breast cancer in a subject. The method can include detecting a single nucleotide polymorphism (SNP) at position 4 of the let-7 complementary site 6 of KRAS in a patient sample wherein the presence of said SNP indicates an increased risk of developing a second, independent cancer in said subject.

4 Claims, 10 Drawing Sheets

Specification includes a Sequence Listing.

(56) References Cited

OTHER PUBLICATIONS

Broeks et al., "Excess risk for contralateral breast cancer in CHEK2*1100delC germline mutation carriers," Breast Cancer Research and Treatment (2004), vol. 83, No. 1, pp. 91-93.
Brooks et al., "Body mass index and risk of second primary breast cancer: The WECARE Study," Breast Cancer Research and Treatment, (2012) vol. 131, No. 2, pp. 571-580.
Calle et al., "Postmenopausal Hormone Use and Breast Cancer Associations Differ by Hormone Regimen and Histologic Subtype," Cancer, (2009), vol. 115, No. 5, pp. 936-945.
Cerne et al., "KRAS rs61764370 is associated with HER2-overexpressed and poorly-differentiated breast cancer in hormone replacement therapy users: a case control study," BMC Cancer (2012), vol. 12, No. 105, pp. 1-7.
Cerne et al., "Functional variants in CYP1 B1, KRAS and MTHFR genes are associated with shorter telomere length in postmenopausal women," Mechanisms of Ageing and Development (2015), vol. 149, pp. 1-7.
Chen et al., "Epidemiology of Contralateral Breast Cancer," Cancer Epidemiology Biomarkers & Prevention, (1999) vol. 8, No. 10, pp. 855-861.
Chin et al., "A SNP in a let-7 microRNA Complementary Site in the DRAS 3' Untranslated Region Increases Non-Small Cell Lung Cancer Risk," Cancer Research (2008), vol. 68, No. 20, pp. 8535-8540.
Chlebowski et al., "Estrogen Plus Progestin and Breast Cancer Incidence and Mortality in the Women's Health Initiative Observational Study," Journal of the National Cancer Institute, (2013), vol. 105, No. 8. pp. 526-535.
Chung et al., "A 3'-UTR KRAS-variant is associated with cisplatin resistance in patients with recurrent and/or metastatic head and neck squamous cell carcinoma," Annals of Oncology, (2014), vol. 25, pp. 2230-2236.
Clarke et al., "Effects of chemotherapy and hormonal therapy for early breast cancer on recurrence and 15-year survival: an overview of the randomised trails," Lancet (2005), vol. 365, pp. 1687-1717.
Debnath et al., "Morphogenesis and oncogenesis of MCF-10A mammary epithelial acini grown in three-dimensional basement membrane cultures," Methods, (2003), vol. 30, pp. 256-268.
Howe et al., "Women with multiple primary breast cancers diagnosed within a five year period, 1994-1998," Breast Cancer Research and Treatment, (2005), vol. 90, No. 3, pp. 223-232.
Kurian et al., "Second Primary Breast Cancer Occurrence According to Hormone Receptor Status," Journal of the National Cancer Institute, (2009), vol. 101, No. 15, pp. 1058-1065.
Lee et al., "The KRAS-variant and miRNA Expression in RTOG Endometrial Cancer Clinical Trials 9708 and 9905," PLOS ONE (2014), vol. 9, No. 4, e94167, pp. 1-8.
Levi et al., "Second primary cancers in the Vaud and Neuchâtel Cancer Registries," European Journal of Cancer Prevention (2015), vol. 24, No. 2, pp. 150-154.
Liu et al., Transformation of MCF-10A Human Breast Epithelial Cells by Zeranol and Estradiol-17β, The Breast Journal, (2004), vol. 10, No. 6, pp. 514-521.
Lostumbo et al., "Prophylactic mastectomy for the prevention of breast cancer," Cochrane Database Syst Review, (2004), DOI: 10.1002/14651858.CD002748.pub 2, pp. 1-67.
Malone et al., "Population-Based Study of the Risk of Second Primary Contralateral Breast Cancer Associated with Carrying a Mutation in BRCA1 or BRCA2," Journal of Clinical Oncology, (2010), vol. 28, No. 14, pp. 2404-2410.
Marcu et al., "Risk of second primary cancer after breast cancer treatment," European Journal of Cancer Care, (2014), vol. 23, No. 1, pp. 51-64.
Marsa "The Little-Known Genetic Mutation Behind Many Aggressive Cancers," Discover Magazine, Oct. 30, 2014, p. 1-9.
McVeigh et al. (2015) "Estrogen withdrawal, increased breast cancer risk and the KRAS-variant," Cell Cycle 14(13):2091-2099.
Metcalfe et al., "Predictors of contralateral breast cancer in BRCA1 and BRCA2 mutation carriers," British Journal of Cancer, (2011), vol. 104, No. 9, pp. 1384-1392.
Mungenast et al., "Estrogen Biosynthesis and Action in Ovarian Cancer," Frontiers in Endocrinology, (2014), vol. 5, pp. 1-12.
Narod, "Bilateral breast cancers," Nature Reviews Clinical Oncology (2014), vol. 11, No. 3, pp. 157-166.
Ness et al. "Risk of Ovarian Cancer in Relation to Estrogen and Progestin Dose and Use Characteristics of Oral Contraceptives," American Journal of Epidemiology, (2000), vol. 152, pp. 233-241.
Paranjape et al., "A 3'-untranslated region KRAS variant and triple-negative breast cancer: a case-control and genetic analysis," The Lancet Oncology, (2011), vol. 12, No. 4, pp. 377-386.
Pilarski et al., "The KRAS-Variant is Associated with Risk of Developing Double Primary Breast and Ovarian Cancer," PLos ONE (2012), vol. 7, Issue 5, e37891, pp. 1-5.
Ratner et al., "A KRAS-Variant in Ovarian Cancer Acts as a Genetic Marker of Cancer Risk," Cancer Research, (2010), vol. 15, pp. 6509-6515.
Ratner et al., "A KRAS variant is a biomarker of poor outcome, platinum chemotherapy resistance and a potential target for therapy in ovarian cancer," Oncogene (2012), vol. 31, No. 42, pp. 4559-4566.
Raymond et al., "Multiple primary tumours in women following breast cancer, 1973-2000," British Journal of Cancer (2006), vol. 94, No. 11, pp. 1745-1750.
Reiner et al., "Risk of Asynchronous Contralateral Breast Cancer in Noncarriers of BRCA1 and BRCA2 Mutations with a Family History of Breast Cancer: A Report from the Women's Environmental Cancer and Radiation Epidemiology Study," Journal of Clinical Oncology (2013), vol. 31, No. 4, pp. 433-439.
Salzman et al., "Making 'silent' mutations speak up." Nature Medicine, (2011), vol. 17, No. 8, pp. 934-935.
Soule et al., "Isolation and Characterization of a Spontaneously Immortalized Human Breast Epithelial Cell Line, MCF-10," Cancer Research, (1990), vol. 50, pp. 6075-6086.
International Search Report and Written Opinion in PCT/US2015/65363 dated Mar. 25, 2016, 11 pages.
Urnov et al., "Highly efficient endogenous human gene correction using designed zinc-finger nucleases," Nature (2005), vol. 435, pp. 646-651.
Wang et al., "Aromatase overexpression induces malignant changes in estrogen receptor a negative MCF-10A cells," Oncogene (2013), 32(44):5233-5240.
Weidhaas "Our Next Study: How Does Breast Cancer Treatment Impact Second Breast Cancer Risk?" MiraKind Blog Jul. 10, 2014 <http://mirakind.org/foundermessage>.
Weidhaas et al., "The KRAS-variant and treatment response in BATTLE-1," J Clin Oncol (2014), vol. 32, No. 52, suppl; abstr 8135.
Extended Search Report for European Patent Application No. 15868577.6 dated Jun. 20, 2018, 9 pages.
Reese et al., "Anastrozole in the management of breast cancer," Expert Opinion on Pharmacotherapy, vol. 3, No. 9, (2002), pp. 1329-1339.
Cipollini, et al., "MicroRNA binding site polymorphisms as biomarkers in cancer management and research," Pharmacogenomics and Personalized Medicine, (2014), vol. 7, pp. 173-191.
Dai, et al., "Let-7 Sensitizes KRAS Mutant Tumor Cells to Chemotherapy," PLOS ONE, (May 2015), 20 pages.
Saridaki et al., "A let-7 microRNA-binding site polymorphism in KRAS predicts improved outcome in metastatic colorectal cancer (mCRC) patients treated with salvage cetuximab/panitumumab monotherapy," Clin Cancer Res., (Sep. 2014), vol. 20, No. 17, pp. 4499-4510.
Sweasy, et al., "Expression of DNA polymerase β cancer-associated variants in mouse cells results in cellular transformation," PNAS, (Oct. 2005), vol. 102, No. 40, pp. 14350-14355.

* cited by examiner

METHODS FOR TREATING OR PREVENTING CANCER IN A KRAS-VARIANT PATIENT AND FOR DIAGNOSING RISK OF DEVELOPING MULTIPLE PRIMARY BREAST TUMORS

CROSS REFERENCE TO RELATED APPLICATIONS

This application is a U.S. National Stage Application filed under 35 U.S.C. § 371 of International Patent Application No. PCT/US2015/065363, filed Dec. 11, 2015, which claims the benefit of and priority to U.S. Provisional Patent Application No. 62/091,357, filed Dec. 12, 2014, the entire contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jun. 19, 2017, is named MIR-001_SL.txt and is 31,903 bytes in size.

BACKGROUND

The KRAS-variant is a biologically functional, microRNA binding site variant in the KRAS oncogene, which predicts increased cancer risk especially for women. MicroRNA (miRNA) binding site variants in the 3' untranslated region (3'UTR) of important growth and survival genes are a recently discovered novel class of germ-line mutations, which are powerful biomarkers of cancer risk and treatment response (Cipollini et al. (2014) Pharmacogenetics and Personalized Medicine 7:173-191).

One of the first mutations discovered in this class is the KRAS-variant, a let-7 binding site mutation in the 3'UTR of the KRAS oncogene (Chin et al. (2008) Cancer Res 68:8535-40). This mutation predicts an increased risk of several cancers, including non-small cell lung cancer (Id.), triple negative breast cancer (TNBC) in premenopausal women (Paranjape et al. (2011) The Lancet Oncology 12(4):377-386) and ovarian cancer (Ratner et al. (2010) Cancer Research 15:6509-15; Ratner et al. (2012) Oncogene 31(42): 4559-66; Pilarski et al. (2012) PLos ONE 7(5):e37891). The KRAS-variant has also been shown to predict unique tumor biology, with tumors in KRAS-variant patients exhibiting a KRAS-addicted signature as well as an estrogen-negative, basal-like gene expression pattern (Ratner, 2012, supra; Paranjape, supra). Women with the KRAS-variant have also been found to be at a significantly increased risk of developing multiple primary cancers, including breast and ovarian cancer, as well as a third independent cancer in the same individual (Pilarski, supra).

Women with the KRAS-variant are also at a significantly increased risk of developing multiple primary cancers, including breast and ovarian cancer, as well as a third independent cancer in their lifetime (Pilarski, supra). Multiple primary cancer, although difficult to predict, is not rare, as up to one in eight cancer patients will be diagnosed with a new primary cancer after their first cancer diagnosis (metachronous cancer), and one in forty patients will be diagnosed with two cancers at the same time (synchronous cancer) (Levi et al. (2014) Eur J Cancer Prev doi: 10.1097/CEJ.0000000000000085). While it is hypothesized that metachronous cancers may be caused by primary cancer treatment, it is also thought that genetics plays a significant role in the development of both synchronous and metachronous cancers (Bhatia (2014) Cancer. doi: 10.1002/cncr.29096; Amer (2014) Cancer Manag Res 5:119-34). Multiple primary breast cancer (MPBC) is one of the most common forms of multiple primary cancer (Howe et al. (2005) Breast Cancer Res Treat 90(3):223-232), yet it remains difficult to identify those at risk. Currently identified risk factors for the development of multiple or bilateral primary breast cancers include young age at first diagnosis (Raymond et al. (2006) British Journal of Cancer 94(11): 1745-1750; Marcu et al. (2014) European Journal of Cancer Care 23(1):51-64; Kurian et al. (2009) Journal of the National Cancer Institute 101(15):1058-1065); first BC of lobular histology (Howe, supra; Chen et al. (1999) Cancer Epidemiol Biomarkers Prev 8(10):855-61; Narod (2014) Nature Reviews Clinical Oncology 11(3):157-166); high BMI (>30) in pre-menopausal patients with a hormone-receptor negative first primary (Brooks et al. (2012) Breast Cancer Res Treat 131(2):571-580); positive family history of breast cancer (Reiner et al. (2013) Journal of Clinical Oncology 31(4):433-439); and mutations in BRCA 1, BRCA 2 (Malone et al. (2010) Journal of Clinical Oncology 28(14): 2404-2410; Metcalfe et al. (2011) British Journal of Cancer 104(9):1384-1392) or CHEK 2 (Broeks et al. (2004) Breast Cancer Res Treat 83(1):91-3). Additionally, in a small case series, the KRAS-variant was found in 57.1% of uninformative (BRCA negative) patients who developed bilateral breast cancer and ovarian cancer (Pilarski, supra). Factors decreasing multiple primary breast cancer risk have also been identified, and include menarche after 13 years of age, multiparity (Narod, supra), treatment with anti-hormonal agents or chemotherapy (Clarke et al. (2005) Lancet 365 (9472):1687-717; Alkner et al. (2009) Eur J Cancer 45(14): 2496-502) and prophylactic surgical intervention (Metcalfe, supra; Lostumbo et al. (2004) Cochrane Database Syst Rev (4):Cd002748). These findings indicate that second BC risk can be impacted by estrogen alterations either before or after the first BC diagnosis.

Evidence that estrogen exposure increases primary breast cancer risk includes increased BC risk in women experiencing early menarche, late menopause, obesity, nulliparity or advanced maternal age at first birth (Anderson et al. (2014) Breast Cancer Research and Treatment 144(1):1-10). In addition, in vitro studies using the breast epithelial line MCF10A support the hypothesis that excess estrogen and its metabolites can lead to increased transformation, or breast cancer initiation (Liu et al. (2004) Breast Journal 10(6): 514-521; Wang et al. (2013) Oncogene 32(44):5233-5240). However, it appears that estrogen is not a risk for breast cancer for all women, as has come to light through data surrounding hormone replacement therapy use (HRT) (Beral (2003) Lancet 362(9382):419-427; Chlebowski et al. (2013) Journal of the National Cancer Institute 105(8):526-535). Initially, the Million Women Study and Women's Health Initiative reported that current and/or prolonged use of HRT correlated with an increased risk of breast cancer. Because these tumors tended to be lower grade, with over-representation of lobular or tubular subtypes compared to other ductal cancers (Calle et al. (2009) Cancer 115(5):936-45), it was hypothesized that HRT was causing cancers that otherwise would not have arisen. However, a follow-up WHI report found that there was actually no increased breast cancer risk for patients assigned to estrogen-only preparations compared to placebo (Anderson et al. (2004) JAMA 291(14):1701-12). In fact, after a median follow up of 11.8 years (IQR 9.1-12.9), post-menopausal use of estrogen alone was associated with a lower breast cancer incidence than placebo (HR 0.77 (CI 0.62-0.95, p 0.02)) (Id.).

For women with the KRAS-variant, there is growing evidence that estrogen may differentially impact their overall cancer risk and tumor biology. This includes: a higher risk of non-small cell lung cancer for women versus men with the KRAS-variant (unpublished data); ovarian cancer risk almost exclusively in post-menopausal women with the KRAS-variant (Pilarski, supra); in increased risk of estrogen receptor (ER) negative tumor development in KRAS-variant patients (TNBC (Paranj ape, supra) and type II uterine cancer (Lee et al. (2014) PLos ONE, 9(4):e94167), and; evidence that KRAS-variant post-menopausal breast cancer patients with a history of HRT are significantly more likely to develop biologically aggressive breast cancer (Cerne et al. (2012) BMC Cancer 12(105)). These findings suggest that estrogen alterations may differentially impact the KRAS-variant, and, there is in fact strong evidence that such miRNA binding site mutations are "influenced" by external exposure (Salzman et al. (2011) Nat Med 17:934-5). This is believed to be through alterations in miRNAs, which are the immediate responders to cellular stress, and which directly act through the 3'UTR sites affected by these mutations (Id.).

Substantial evidence that the KRAS-variant acts as a cancer biomarker of response to therapy also exists. This includes cisplatin resistance in KRAS-variant patients with ovarian or head and neck cancer (Rather, 2012, supra; Chung et al. (2014) Ann Oncol, July 31. [Epub ahead of printing]), cetuximab sensitivity in KRAS-variant patients with colon cancer (Saridaki et al. (2014) Clin Cancer Res 20(17):4499-510) or head and neck cancer (Chung, supra), and erlotonib resistance but sorafenib sensitivity in KRAS-variant patients with non-small cell lung cancer (NSCLC) (Weidhaas et al. (2014) J Clin Oncol 32(52):suppl; abstr 8135). Cell line data further supports the unique response of the KRAS-variant to chemotherapy exposures (Saridaki, supra).

Accordingly, there is a need in the art for methods to prevent and treat cancer in subjects with KRAS-variant. In addition, there is a need in the art for methods to predict who is at risk for the development of second primary breast tumors, so that preventative measures can be taken and treatment appropriately administered.

SUMMARY OF THE INVENTION

The present invention relates to the discovery that for women with the KRAS-variant, estrogen withdrawal appears to increase risk for both tumor development as well as aggressive breast cancer tumor biology, both in vivo and in vitro. The present invention relates to the further discovery that KRAS-variant breast cancer patients are at a significantly elevated risk for both synchronous and asynchronous second breast cancer development, which is not otherwise explained by other known risk factors.

Accordingly, the present invention relates to methods for preventing cancer in a KRAS-variant subject which include administering to the KRAS-variant subject an amount of estrogen effective to reduce the risk of developing cancer. For example, the method may include administering to a KRAS-variant subject a tapering dose of estrogen, starting with the patient's pre-oophorectomy baseline estrogen levels, or pre-chemotherapy estrogen levels, which can be calculated. In certain embodiments, the method may include administering HRT to an oophorectomy patient to compensate for the sudden loss in estrogen that occurs with ovary removal, and gradually decreasing the HRT dose over time. In certain embodiments, estrogen is administered at about 0.01 mg/kg to about 0.1 mg/kg, and the dosage is decreased over time.

In another aspect, the invention relates to methods for treating cancer in a KRAS-variant subject, which include reducing estrogen activity in the KRAS-variant subject to reduce the risk of aggressive tumor growth. In certain embodiments, estrogen exposure is gradually decreased by antagonizing estrogen function, for example, by administering an estrogen antagonist or an estrogen receptor antagonist. In certain embodiments, the estrogen receptor antagonist is tamoxifen. The tamoxifen may be administered at 10 or 20 mg twice a day or at 10 or 20 mg once daily. Administration may continue for three months, six months, one year, two years, three years, four years, five years, or indefinitely. In certain embodiments, the estrogen receptor antagonist is a selective estrogen receptor modulator (SERM) or selective estrogen receptor down-regulator (SERD). In certain embodiments, the SERM is clomifene, femarelle, ormeloxifene, raloxifene, toremifene, lasofoxifene, ospemifene, afimoxifene, arzoxifene or bazedoxifene. In certain embodiments, the SERD is fulvestrant (Faslodex®). Any dosage of the estrogen antagonist or estrogen receptor antagonist known in the art may be used. Administration of the estrogen antagonist or estrogen receptor antagonist may continue for three months, six months, one year, two years, three years, four years, five years, or indefinitely.

In any of the above embodiments, the cancer may be breast cancer, uterine cancer or ovarian cancer. In any of the above embodiments, the method further comprises detecting a single nucleotide polymorphism (SNP) at position 4 of the let-7 complementary site 6 of KRAS in a patient sample wherein the presence of said SNP indicates an increased risk of developing cancer in said subject.

In another aspect, the invention relates to a method of predicting an increased risk of developing a second, independent breast cancer in a subject. The method includes detecting a single nucleotide polymorphism (SNP) at position 4 of the let-7 complementary site 6 of KRAS in a patient sample wherein the presence of said SNP indicates an increased risk of developing a second, independent cancer in said subject. In certain embodiments, the second, independent cancer is breast cancer. In certain embodiments, the subject is a breast cancer patient.

DETAILED DESCRIPTION

A. Introduction

Figure 1A:
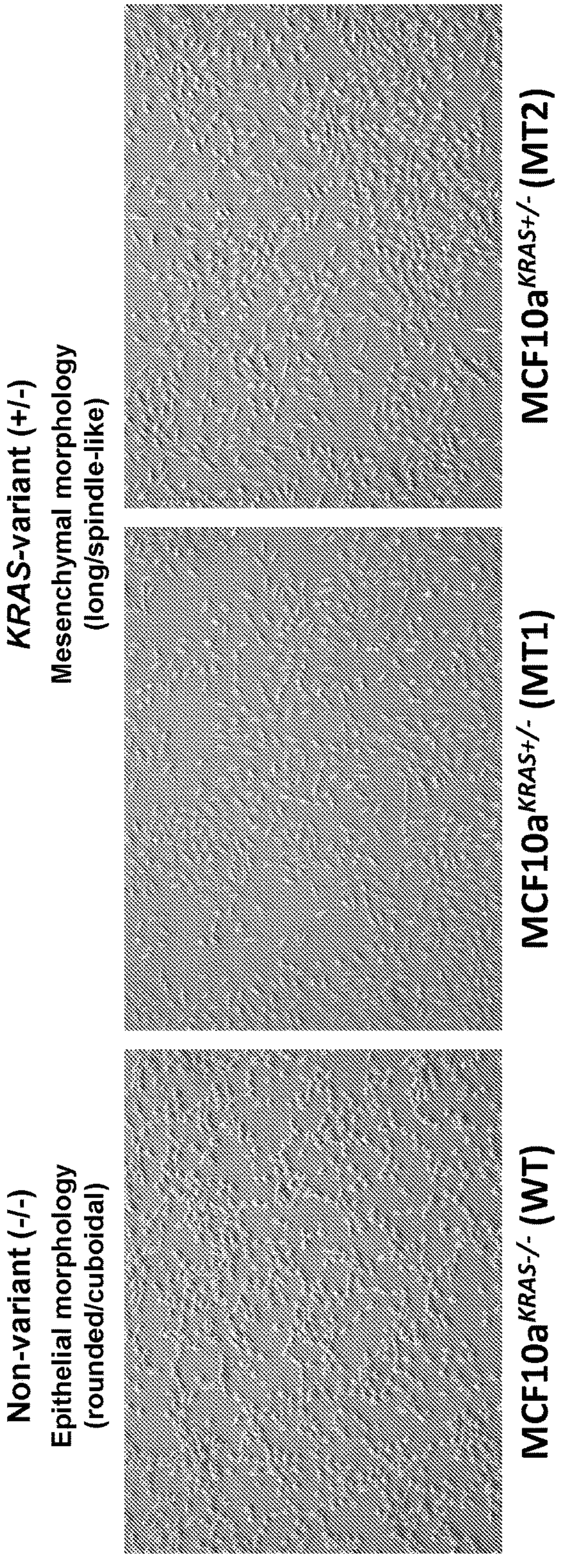
FIG. 1A shows isogenic non-variant and KRAS-variant MCF10a cell lines grown on epidermal growth factor (EGF). Non-variant cells showed rounded/cuboidal epithelial morphology, while KRAS-variant lines exhibited a mesenchymal spindle phenotype, suggesting a baseline epithelial to mesenchymal transition in the presence of the KRAS-variant.

The KRAS-variant, a SNP in the 3' untranslated region (UTR) of KRAS, referred to herein as the "LCS6 SNP," or the "KRAS-variant," is a germ-line, dynamically regulated microRNA binding site mutation in the KRAS oncogene, which predicts increased cancer risk primarily in women, multiple cancer risk in the same patient, and tumor biology across cancer types. The KRAS-variant has been previously shown to be a genetic marker of increased risk of triple negative breast cancer and to predict aggressive breast tumor biology with hormone replacement therapy use.

The invention is based upon the unexpected discovery that for women with the KRAS-variant, estrogen withdrawal appears to increase risk for both tumor development as well as aggressive breast cancer tumor biology, both in vivo and in vitro. Further, the invention relates to the unexpected discovery that KRAS-variant breast cancer patients are at a significantly elevated risk for both synchronous and asynchronous second breast cancer development, which is not otherwise explained by other known risk factors.

There are three human RAS genes comprising HRAS, KRAS, and NRAS. Each gene comprises multiple miRNA complementary sites in the 3'UTR of their mRNA transcripts. Specifically, each human RAS gene comprises multiple let-7 complementary sites (LCSs). The let-7 family-of-microRNAs (miRNAs) are global genetic regulators important in controlling lung cancer oncogene expression by binding to the 3'UTRs (untranslated regions) of their target messenger RNAs (mRNAs).

Specifically, the term "let-7 complementary site" is meant to describe any region of a gene or gene transcript that binds a member of the let-7 family of miRNAs. Moreover, this term encompasses those sequences within a gene or gene transcript that are complementary to the sequence of a let-7 family miRNA. The term "complementary" describes a threshold of binding between two sequences wherein a majority of nucleotides in each sequence are capable of binding to a majority of nucleotides within the other sequence in trans.

The Human KRAS 3' UTR comprises 8 LCSs named LCS1-LCS8, respectively. For the following sequences, thymine (T) may be substituted for uracil (U). LCS1 comprises the sequence GACAGUGGAAGUUUUUUUUUCCUCG (SEQ ID NO: 1). LCS2 comprises the sequence AUUAGUGUCAUCUUGCCUC (SEQ ID NO: 2). LCS3 comprises the sequence AAUGCCCUACAUCUUAUUUUCCUCA (SEQ ID NO: 3). LCS4 comprises the sequence GGUUCAAGCGAUUCUCGUGCCUCG (SEQ ID NO: 4). LCS5 comprises the sequence GGCUGGUCCGAACUCCUGACCUCA (SEQ ID NO: 5). LCS6 comprises the sequence GAUUCACCCACCUUGGCCUCA (SEQ ID NO: 6). LCS7 comprises the sequence GGGUGUUAAGACUUGACACAGUACCUCG (SEQ ID NO: 7). LCS8 comprises the sequence AGUGCUUAUGAGGGGAUAUUUAGGCCUC (SEQ ID NO: 8).

Human KRAS has two wild type forms, encoded by transcripts a and b, which provided below as SEQ ID NOs: 9 and 10, respectively. The sequences of each human KRAS transcript, containing the LCS6 SNP (KRAS-variant), are provided below as SEQ ID NOs: 11 and 12.

Human KRAS, transcript variant a, is encoded by the following mRNA sequence (NCBI Accession No. NM_033360 and SEQ ID NO: 9) (untranslated regions are bolded, LCS6 is underlined):

```
  1 ggccgcggcg gcggaggcag cagcggcggc ggcagtggcg gcggcgaagg tggcggcggc
 61 tcggccagta ctcccggccc ccgccatttc ggactgggag cgagcgcggc gcaggcactg
121 aaggcggcgg cggggccaga ggctcagcgg ctcccaggtg cgggagagag gcctgctgaa
181 aatgactgaa tataaacttg tggtagttgg agctggtggc gtaggcaaga gtgccttgac
241 gatacagcta attcagaatc attttgtgga cgaatatgat ccaacaatag aggattccta
301 caggaagcaa gtagtaattg atggagaaac ctgtctcttg gatattctcg acacagcagg
```

-continued

```
361 tcaagaggag tacagtgcaa tgagggacca gtacatgagg actggggagg gctttctttg
421 tgtatttgcc ataaataata ctaaatcatt tgaagatatt caccattata gagaacaaat
481 taaaagagtt aaggactctg aagatgtacc tatggtccta gtaggaaata aatgtgattt
541 gccttctaga acagtagaca caaaacaggc tcaggactta gcaagaagtt atggaattcc
601 ttttattgaa acatcagcaa agacaagaca gagagtggag gatgcttttt atacattggt
661 gagggagatc cgacaataca gattgaaaaa aatcagcaaa gaagaaaaga ctcctggctg
721 tgtgaaaatt aaaaaatgca ttataatgta atctgggtgt tgatgatgcc ttctatacat
781 tagttcgaga aattcgaaaa cataaagaaa agatgagcaa agatggtaaa aagaagaaaa
841 agaagtcaaa gacaaagtgt gtaattatgt aaatacaatt tgtacttttt tcttaaggca
901 tactagtaca agtggtaatt tttgtacatt acactaaatt attagcattt gttttagcat
961 tacctaattt ttttcctgct ccatgcagac tgttagcttt taccttaaat gcttatttta
1021 aaatgacagt ggaagttttt ttttcctcta agtgccagta ttcccagagt tttggttttt
1081 gaactagcaa tgcctgtgaa aaagaaactg aatacctaag atttctgtct tggggttttt
1141 ggtgcatgca gttgattact tcttattttt cttaccaatt gtgaatgttg gtgtgaaaca
1201 aattaatgaa gcttttgaat catccctatt ctgtgtttta tctagtcaca taaatggatt
1261 aattactaat ttcagttgag accttctaat tggtttttac tgaaacattg agggaacaca
1321 aatttatggg cttcctgatg atgattcttc taggcatcat gtcctatagt ttgtcatccc
1381 tgatgaatgt aaagttacac tgttcacaaa ggttttgtct cctttccact gctattagtc
1441 atggtcactc tccccaaaat attatatttt ttctataaaa agaaaaaaat ggaaaaaaat
1501 tacaaggcaa tggaaactat tataaggcca tttccttttc acattagata aattactata
1561 aagactccta atagcttttc ctgttaaggc agacccagta tgaaatgggg attattatag
1621 caaccatttt ggggctatat ttacatgcta ctaaattttt ataataattg aaaagatttt
1681 aacaagtata aaaaattctc ataggaatta aatgtagtct ccctgtgtca gactgctctt
1741 tcatagtata actttaaatc ttttcttcaa cttgagtctt tgaagatagt tttaattctg
1801 cttgtgacat taaaagatta tttgggccag ttatagctta ttaggtgttg aagagaccaa
1861 ggttgcaagg ccaggccctg tgtgaacctt tgagctttca tagagagttt cacagcatgg
1921 actgtgtccc cacggtcatc cagtgttgtc atgcattggt tagtcaaaat ggggagggac
1981 tagggcagtt tggatagctc aacaagatac aatctcactc tgtggtggtc ctgctgacaa
2041 atcaagagca ttgcttttgt ttcttaagaa aacaaactct tttttaaaaa ttacttttaa
2101 atattaactc aaaagttgag attttggggt ggtggtgtgc caagacatta attttttttt
2161 taaacaatga agtgaaaaag ttttacaatc tctaggtttg gctagttctc ttaacactgg
2221 ttaaattaac attgcataaa cacttttcaa gtctgatcca tatttaataa tgctttaaaa
2281 taaaaataaa aacaatcctt ttgataaatt taaaatgtta cttattttaa aataaatgaa
2341 gtgagatggc atggtgaggt gaaagtatca ctggactagg aagaaggtga cttaggttct
2401 agataggtgt cttttaggac tctgattttg aggacatcac ttactatcca tttcttcatg
2461 ttaaaagaag tcatctcaaa ctcttagttt tttttttta caactatgta atttatattc
2521 catttacata aggatacact tatttgtcaa gctcagcaca atctgtaaat ttttaaccta
2581 tgttacacca tcttcagtgc cagtcttggg caaaattgtg caagaggtga agtttatatt
2641 tgaatatcca ttctcgtttt aggactcttc ttccatatta gtgtcatctt gcctccctac
2701 cttccacatg ccccatgact tgatgcagtt ttaatacttg taattcccct aaccataaga
2761 tttactgctg ctgtggatat ctccatgaag ttttcccact gagtcacatc agaaatgccc
```

-continued

```
2821 tacatcttat ttcctcaggg ctcaagagaa tctgacagat accataaagg gatttgacct
2881 aatcactaat tttcaggtgg tggctgatgc tttgaacatc tctttgctgc ccaatccatt
2941 agcgacagta ggatttttca aacctggtat gaatagacag aaccctatcc agtggaagga
3001 gaatttaata aagatagtgc tgaaagaatt ccttaggtaa tctataacta ggactactcc
3061 tggtaacagt aatacattcc attgttttag taaccagaaa tcttcatgca atgaaaaata
3121 ctttaattca tgaagcttac tttttttttt tggtgtcaga gtctcgctct tgtcacccag
3181 gctggaatgc agtggcgcca tctcagctca ctgcaacctc catctcccag gttcaagcga
3241 ttctcgtgcc tcggcctcct gagtagctgg gattacaggc gtgtgccact acactcaact
3301 aatttttgta tttttaggag agacggggtt tcaccctgtt ggccaggctg gtctcgaact
3361 cctgacctca agtgattcac ccaccttggc ctcataaacc tgttttgcag aactcattta
3421 ttcagcaaat atttattgag tgcctaccag atgccagtca ccgcacaagg cactgggtat
3481 atggtatccc caaacaagag acataatccc ggtccttagg tagtgctagt gtggtctgta
3541 atatcttact aaggcctttg gtatacgacc cagagataac acgatgcgta ttttagtttt
3601 gcaaagaagg ggtttggtct ctgtgccagc tctataattg ttttgctacg attccactga
3661 aactcttcga tcaagctact ttatgtaaat cacttcattg ttttaaagga ataaacttga
3721 ttatattgtt tttttatttg gcataactgt gattctttta ggacaattac tgtacacatt
3781 aaggtgtatg tcagatattc atattgaccc aaatgtgtaa tattccagtt ttctctgcat
3841 aagtaattaa aatatactta aaaattaata gttttatctg ggtacaaata aacaggtgcc
3901 tgaactagtt cacagacaag gaaacttcta tgtaaaaatc actatgattt ctgaattgct
3961 atgtgaaact acagatcttt ggaacactgt ttaggtaggg tgttaagact tacacagtac
4021 ctcgtttcta cacagagaaa gaaatggcca tacttcagga actgcagtgc ttatgagggg
4081 atatttaggc ctcttgaatt tttgatgtag atgggcattt ttttaaggta gtggttaatt
4141 acctttatgt gaactttgaa tggtttaaca aaagatttgt ttttgtagag attttaaagg
4201 gggagaattc tagaaataaa tgttacctaa ttattacagc cttaaagaca aaaatccttg
4261 ttgaagtttt tttaaaaaaa gctaaattac atagacttag gcattaacat gtttgtggaa
4321 gaatatagca gacgtatatt gtatcatttg agtgaatgtt cccaagtagg cattctaggc
4381 tctatttaac tgagtcacac tgcataggaa tttagaacct aacttttata ggttatcaaa
4441 actgttgtca ccattgcaca attttgtcct aatatataca tagaaacttt gtggggcatg
4501 ttaagttaca gtttgcacaa gttcatctca tttgtattcc attgattttt tttttcttct
4561 aaacattttt tcttcaaaca gtatataact ttttttaggg gatttttttt tagacagcaa
4621 aaactatctg aagatttcca tttgtcaaaa agtaatgatt tcttgataat tgtgtagtaa
4681 tgtttttttag aacccagcag ttaccttaaa gctgaattta tatttagtaa cttctgtgtt
4741 aatactggat agcatgaatt ctgcattgag aaactgaata gctgtcataa aatgaaactt
4801 tctttctaaa gaaagatact cacatgagtt cttgaagaat agtcataact agattaagat
4861 ctgtgtttta gtttaatagt ttgaagtgcc tgtttgggat aatgataggt aatttagatg
4921 aatttagggg aaaaaaaagt tatctgcaga tatgttgagg gcccatctct ccccccacac
4981 ccccacagag ctaactgggt tacagtgttt tatccgaaag tttccaattc cactgtcttg
5041 tgttttcatg ttgaaaatac ttttgcattt ttcctttgag tgccaatttc ttactagtac
5101 tatttcttaa tgtaacatgt ttacctggaa tgtattttaa ctatttttgt atagtgtaaa
5161 ctgaaacatg cacattttgt acattgtgct ttcttttgtg ggacatatgc agtgtgatcc
```

-continued

5221 agttgttttc catcatttgg ttgcgctgac ctaggaatgt tggtcatatc aaacattaaa

5281 aatgaccact cttttaattg aaattaactt ttaaatgttt ataggagtat gtgctgtgaa

5341 gtgatctaaa atttgtaata tttttgtcat gaactgtact actcctaatt attgtaatgt

5401 aataaaaata gttacagtga caaaaaaaaa aaaaaa

Human KRAS, transcript variant b, is encoded by the following mRNA sequence (NCBI Accession No. NM_004985 and SEQ ID NO: 10) (untranslated regions are bolded, LCS6 is underlined):

1 ggccgcggcg gcggaggcag cagcggcggc ggcagtggcg gcggcgaagg tggcggcggc

61 tcggccagta ctcccggccc ccgccatttc ggactgggag cgagcgcggc gcaggcactg

121 aaggcggcgg cggggccaga ggctcagcgg ctcccaggtg cgggagagag gcctgctgaa

181 aatgactgaa tataaacttg tggtagttgg agctggtggc gtaggcaaga gtgccttgac 241 gatacagcta attcagaatc attttgtgga cgaatatgat ccaacaatag aggattccta 301 caggaagcaa gtagtaattg atggagaaac ctgtctcttg gatattctcg acacagcagg 361 tcaagaggag tacagtgcaa tgagggacca gtacatgagg actggggagg gctttctttg 421 tgtatttgcc ataaataata ctaaatcatt tgaagatatt caccattata gagaacaaat 481 taaaagagtt aaggactctg aagatgtacc tatggtccta gtaggaaata aatgtgattt 541 gccttctaga acagtagaca caaaacaggc tcaggactta gcaagaagtt atggaattcc 601 ttttattgaa acatcagcaa agacaagaca gggtgttgat gatgccttct atacattagt 661 tcgagaaatt cgaaaacata aagaaaagat gagcaaagat ggtaaaaaga agaaaaagaa 721 gtcaaagaca aagtgtgtaa ttatgtaaat acaatttgta ctttttttctt aaggcatact

781 agtacaagtg gtaatttttg tacattacac taaattatta gcatttgttt tagcattacc

841 taattttttt cctgctccat gcagactgtt agcttttacc ttaaatgctt attttaaaat

901 gacagtggaa gttttttttt cctctaagtg ccagtattcc cagagttttg gtttttgaac

961 tagcaatgcc tgtgaaaaag aaactgaata cctaagattt ctgtcttggg gtttttggtg

1021 catgcagttg attacttctt atttttctta ccaattgtga atgttggtgt gaaacaaatt

1081 aatgaagctt ttgaatcatc cctattctgt gttttatcta gtcacataaa tggattaatt

1141 actaatttca gttgagacct tctaattggt ttttactgaa acattgaggg aacacaaatt

1201 tatgggcttc ctgatgatga ttcttctagg catcatgtcc tatagtttgt catccctgat

1261 gaatgtaaag ttacactgtt cacaaaggtt ttgtctcctt tccactgcta ttagtcatgg

1321 tcactctccc caaaatatta tatttttttct ataaaaagaa aaaaatggaa aaaaattaca

1381 aggcaatgga aactattata aggccatttc cttttcacat tagataaatt actataaaga

1441 ctcctaatag cttttcctgt taaggcagac ccagtatgaa atggggatta ttatagcaac

1501 cattttgggg ctatatttac atgctactaa atttttataa taattgaaaa gattttaaca

1561 agtataaaaa attctcatag gaattaaatg tagtctccct gtgtcagact gctctttcat

1621 agtataactt taaatctttt cttcaacttg agtctttgaa gatagtttta attctgcttg

1681 tgacattaaa agattatttg ggccagttat agcttattag gtgttgaaga gaccaaggtt

1741 gcaaggccag gccctgtgtg aacctttgag ctttcataga gagtttcaca gcatggactg

1801 tgtccccacg gtcatccagt gttgtcatgc attggttagt caaaatgggg agggactagg

1861 gcagtttgga tagctcaaca agatacaatc tcactctgtg gtggtcctgc tgacaaatca

1921 agagcattgc ttttgtttct taagaaaaca aactcttttt taaaaattac ttttaaatat

-continued 1981 taactcaaaa gttgagattt tggggtggtg gtgtgccaag acattaattt tttttttaaa 2041 caatgaagtg aaaaagtttt acaatctcta ggtttggcta gttctcttaa cactggttaa 2101 attaacattg cataaacact tttcaagtct gatccatatt taataatgct ttaaaataaa 2161 aataaaaaca atccttttga taaatttaaa atgttactta ttttaaaata aatgaagtga 2221 gatggcatgg tgaggtgaaa gtatcactgg actaggaaga aggtgactta ggttctagat 2281 aggtgtcttt taggactctg attttgagga catcacttac tatccatttc ttcatgttaa 2341 aagaagtcat ctcaaactct tagttttttt tttttacaac tatgtaattt atattccatt 2401 tacataagga tacacttatt tgtcaagctc agcacaatct gtaaattttt aacctatgtt 2461 acaccatctt cagtgccagt cttgggcaaa attgtgcaag aggtgaagtt tatatttgaa 2521 tatccattct cgttttagga ctcttcttcc atattagtgt catcttgcct ccctaccttc 2581 cacatgcccc atgacttgat gcagttttaa tacttgtaat tcccctaacc ataagattta 2641 ctgctgctgt ggatatctcc atgaagtttt cccactgagt cacatcagaa atgccctaca 2701 tcttatttcc tcagggctca agagaatctg acagatacca taaagggatt tgacctaatc 2761 actaatttcc aggtggtggc tgatgctttg aacatctctt tgctgcccaa tccattagcg 2821 acagtaggat ttttcaaacc tggtatgaat agacagaacc ctatccagtg gaaggagaat 2881 ttaataaaga tagtgctgaa agaattcctt aggtaatcta taactaggac tactcctggt 2941 aacagtaata cattccattg ttttagtaac cagaaatctt catgcaatga aaaatacttt 3001 aattcatgaa gcttactttt ttttttggt gtcagagtct cgctcttgtc acccaggctg 3061 gaatgcagtg gcgccatctc agctcactgc aacctccatc tcccaggttc aagcgattct 3121 cgtgcctcgg cctcctgagt agctgggatt acaggcgtgt gccactacac tcaactaatt 3181 tttgtatttt taggagagac ggggtttcac cctgttggcc aggctggtct cgaactcctg 3241 acctcaagtg attcacccac cttggcctca taaacctgtt ttgcagaact catttattca 3301 gcaaatattt attgagtgcc taccagatgc cagtcaccgc acaaggcact gggtatatgg 3361 tatccccaaa caagagacat aatcccggtc cttaggtagt gctagtgtgg tctgtaatat 3421 cttactaagg cctttggtat acgacccaga gataacacga tgcgtatttt agttttgcaa 3481 agaaggggtt tggtctctgt gccagctcta taattgtttt gctacgattc cactgaaact 3541 cttcgatcaa gctactttat gtaaatcact tcattgtttt aaaggaataa acttgattat 3601 attgtttttt tatttggcat aactgtgatt cttttaggac aattactgta cacattaagg 3661 tgtatgtcag atattcatat tgacccaaat gtgtaatatt ccagttttct ctgcataagt 3721 aattaaaata tacttaaaaa ttaatagttt tatctgggta caaataaaca ggtgcctgaa 3781 ctagttcaca gacaaggaaa cttctatgta aaaatcacta tgatttctga attgctatgt 3841 gaaactacag atctttggaa cactgtttag gtagggtgtt aagacttaca cagtacctcg 3901 tttctacaca gagaaagaaa tggccatact tcaggaactg cagtgcttat gaggggatat 3961 ttaggcctct tgaatttttg atgtagatgg gcattttttt aaggtagtgg ttaattacct 4021 ttatgtgaac tttgaatggt ttaacaaaag atttgttttt gtagagattt taaaggggga 4081 gaattctaga aataaatgtt acctaattat tacagcctta aagacaaaaa tccttgttga 4141 agttttttta aaaaaagcta aattacatag acttaggcat taacatgttt gtggaagaat 4201 atagcagacg tatattgtat catttgagtg aatgttccca agtaggcatt ctaggctcta 4261 tttaactgag tcacactgca taggaattta gaacctaact tttataggtt atcaaaactg 4321 ttgtcaccat tgcacaattt tgtcctaata tatacataga aactttgtgg ggcatgttaa -continued 4381 gttacagttt gcacaagttc atctcatttg tattccattg attttttttt tcttctaaac

4441 atttttttctt caaacagtat ataacttttt ttaggggatt ttttttttaga cagcaaaaac

4501 tatctgaaga tttccatttg tcaaaaagta atgatttctt gataattgtg tagtaatgtt

4561 ttttagaacc cagcagttac cttaaagctg aatttatatt tagtaacttc tgtgttaata

4621 ctggatagca tgaattctgc attgagaaac tgaatagctg tcataaaatg aaactttctt

4681 tctaaagaaa gatactcaca tgagttcttg aagaatagtc ataactagat taagatctgt

4741 gttttagttt aatagtttga agtgcctgtt tgggataatg ataggtaatt tagatgaatt

4801 taggggaaaa aaaagttatc tgcagatatg ttgagggccc atctctcccc ccacaccccc

4861 acagagctaa ctgggttaca gtgttttatc cgaaagtttc caattccact gtcttgtgtt

4921 ttcatgttga aaatactttt gcatttttcc tttgagtgcc aatttcttac tagtactatt

4981 tcttaatgta acatgtttac ctggaatgta ttttaactat ttttgtatag tgtaaactga

5041 aacatgcaca ttttgtacat tgtgctttct tttgtgggac atatgcagtg tgatccagtt

5101 gttttccatc atttggttgc gctgacctag gaatgttggt catatcaaac attaaaaatg

5161 accactcttt taattgaaat taacttttaa atgtttatag gagtatgtgc tgtgaagtga

5221 tctaaaattt gtaatatttt tgtcatgaac tgtactactc ctaattattg taatgtaata

5281 aaaatagtta cagtgacaaa aaaaaaaaaa aa

Human KRAS, transcript variant a, comprising the LCS6 SNP (KRAS-variant), is encoded by the following mRNA sequence (SEQ ID NO: 11) (untranslated regions are bolded, LCS6 is underlined, SNP is capitalized):

1 ggccgcggcg gcggaggcag cagcggcggc ggcagtggcg gcggcgaagg tggcggcggc

61 tcggccagta ctcccggccc ccgccatttc ggactgggag cgagcgcggc gcaggcactg

121 aaggcggcgg cggggccaga ggctcagcgg ctcccaggtg cgggagagag gcctgctgaa

181 aatgactgaa tataaacttg tggtagttgg agctggtggc gtaggcaaga gtgccttgac 241 gatacagcta attcagaatc attttgtgga cgaatatgat ccaacaatag aggattccta 301 caggaagcaa gtagtaattg atggagaaac ctgtctcttg gatattctcg acacagcagg 361 tcaagaggag tacagtgcaa tgagggacca gtacatgagg actggggagg gctttctttg 421 tgtatttgcc ataaataata ctaaatcatt tgaagatatt caccattata gagaacaaat 481 taaaagagtt aaggactctg aagatgtacc tatggtccta gtaggaaata aatgtgattt 541 gccttctaga acagtagaca caaaacaggc tcaggactta gcaagaagtt atggaattcc 601 ttttattgaa acatcagcaa agacaagaca gagagtggag gatgcttttt atacattggt 661 gagggagatc cgacaataca gattgaaaaa aatcagcaaa gaagaaaaga ctcctggctg 721 tgtgaaaatt aaaaaatgca ttataatgta atctgggtgt tgatgatgcc ttctatacat

781 tagttcgaga aattcgaaaa cataaagaaa agatgagcaa agatggtaaa aagaagaaaa

841 agaagtcaaa gacaaagtgt gtaattatgt aaatacaatt tgtacttttt tcttaaggca

901 tactagtaca agtggtaatt tttgtacatt acactaaatt attagcattt gttttagcat

961 tacctaattt ttttcctgct ccatgcagac tgttagcttt taccttaaat gcttatttta

1021 aaatgacagt ggaagttttt ttttcctcta agtgccagta ttcccagagt tttggttttt

1081 gaactagcaa tgcctgtgaa aaagaaactg aatacctaag atttctgtct tggggttttt

1141 ggtgcatgca gttgattact tcttattttt cttaccaatt gtgaatgttg gtgtgaaaca

1201 aattaatgaa gcttttgaat catccctatt ctgtgtttta tctagtcaca taaatggatt

1261 aattactaat ttcagttgag accttctaat tggtttttac tgaaacattg agggaacaca

-continued 1321 aatttatggg cttcctgatg atgattcttc taggcatcat gtcctatagt ttgtcatccc 1381 tgatgaatgt aaagttacac tgttcacaaa ggttttgtct cctttccact gctattagtc 1441 atggtcactc tccccaaaat attatatttt ttctataaaa agaaaaaaat ggaaaaaaat 1501 tacaaggcaa tggaaactat tataaggcca tttccttttc acattagata aattactata 1561 aagactccta atagcttttc ctgttaaggc agacccagta tgaaatgggg attattatag 1621 caaccatttt ggggctatat ttacatgcta ctaaattttt ataataattg aaaagatttt 1681 aacaagtata aaaaattctc ataggaatta aatgtagtct ccctgtgtca gactgctctt 1741 tcatagtata actttaaatc ttttcttcaa cttgagtctt tgaagatagt tttaattctg 1801 cttgtgacat taaaagatta tttgggccag ttatagctta ttaggtgttg aagagaccaa 1861 ggttgcaagg ccaggccctg tgtgaacctt tgagctttca tagagagttt cacagcatgg 1921 actgtgtccc cacggtcatc cagtgttgtc atgcattggt tagtcaaaat ggggagggac 1981 tagggcagtt tggatagctc aacaagatac aatctcactc tgtggtggtc ctgctgacaa 2041 atcaagagca ttgcttttgt ttcttaagaa aacaaactct tttttaaaaa ttacttttaa 2101 atattaactc aaaagttgag attttggggt ggtggtgtgc caagacatta attttttttt 2161 taaacaatga agtgaaaaag ttttacaatc tctaggtttg gctagttctc ttaacactgg 2221 ttaaattaac attgcataaa cacttttcaa gtctgatcca tatttaataa tgctttaaaa 2281 taaaaataaa aacaatcctt ttgataaatt taaaatgtta cttattttaa aataaatgaa 2341 gtgagatggc atggtgaggt gaaagtatca ctggactagg aagaaggtga cttaggttct 2401 agataggtgt cttttaggac tctgattttg aggacatcac ttactatcca tttcttcatg 2461 ttaaaagaag tcatctcaaa ctcttagttt ttttttttta caactatgta atttatattc 2521 catttacata aggatacact tatttgtcaa gctcagcaca atctgtaaat ttttaaccta 2581 tgttacacca tcttcagtgc cagtcttggg caaaattgtg caagaggtga agtttatatt 2641 tgaatatcca ttctcgtttt aggactcttc ttccatatta gtgtcatctt gcctccctac 2701 cttccacatg ccccatgact tgatgcagtt ttaatacttg taattcccct aaccataaga 2761 tttactgctg ctgtggatat ctccatgaag ttttcccact gagtcacatc agaaatgccc 2821 tacatcttat ttcctcaggg ctcaagagaa tctgacagat accataaagg gatttgacct 2881 aatcactaat tttcaggtgg tggctgatgc tttgaacatc tctttgctgc ccaatccatt 2941 agcgacagta ggatttttca aacctggtat gaatagacag aaccctatcc agtggaagga 3001 gaatttaata aagatagtgc tgaaagaatt ccttaggtaa tctataacta ggactactcc 3061 tggtaacagt aatacattcc attgttttag taaccagaaa tcttcatgca atgaaaaata 3121 ctttaattca tgaagcttac tttttttttt tggtgtcaga gtctcgctct tgtcacccag 3181 gctggaatgc agtggcgcca tctcagctca ctgcaacctc catctcccag gttcaagcga 3241 ttctcgtgcc tcggcctcct gagtagctgg gattacaggc gtgtgccact acactcaact 3301 aatttttgta tttttaggag agacggggtt tcaccctgtt ggccaggctg gtctcgaact 3361 cctgacctca agtgatGcac ccaccttggc ctcataaacc tgttttgcag aactcattta 3421 ttcagcaaat atttattgag tgcctaccag atgccagtca ccgcacaagg cactgggtat 3481 atggtatccc caaacaagag acataatccc ggtccttagg tagtgctagt gtggtctgta 3541 atatcttact aaggcctttg gtatacgacc cagagataac acgatgcgta ttttagtttt 3601 gcaaagaagg ggtttggtct ctgtgccagc tctataattg ttttgctacg attccactga 3661 aactcttcga tcaagctact ttatgtaaat cacttcattg ttttaaagga ataaacttga -continued 3721 ttatattgtt tttttatttg gcataactgt gattctttta ggacaattac tgtacacatt

3781 aaggtgtatg tcagatattc atattgaccc aaatgtgtaa tattccagtt ttctctgcat

3841 aagtaattaa aatatactta aaaattaata gttttatctg ggtacaaata aacaggtgcc

3901 tgaactagtt cacagacaag gaaacttcta tgtaaaaatc actatgattt ctgaattgct

3961 atgtgaaact acagatcttt ggaacactgt ttaggtaggg tgttaagact tacacagtac

4021 ctcgtttcta cacagagaaa gaaatggcca tacttcagga actgcagtgc ttatgagggg

4081 atatttaggc ctcttgaatt tttgatgtag atgggcattt ttttaaggta gtggttaatt

4141 acctttatgt gaactttgaa tggtttaaca aaagatttgt ttttgtagag attttaaagg

4201 gggagaattc tagaaataaa tgttacctaa ttattacagc cttaaagaca aaaatccttg

4261 ttgaagtttt tttaaaaaaa gctaaattac atagacttag gcattaacat gtttgtggaa

4321 gaatatagca gacgtatatt gtatcatttg agtgaatgtt cccaagtagg cattctaggc

4381 tctatttaac tgagtcacac tgcataggaa tttagaacct aacttttata ggttatcaaa

4441 actgttgtca ccattgcaca atttgtcct aatatataca tagaaacttt gtggggcatg

4501 ttaagttaca gtttgcacaa gttcatctca tttgtattcc attgattttt tttttcttct

4561 aaacattttt tcttcaaaca gtatataact ttttttaggg gatttttttt tagacagcaa

4621 aaactatctg aagatttcca tttgtcaaaa agtaatgatt tcttgataat tgtgtagtaa

4681 tgttttttag aacccagcag ttaccttaaa gctgaattta tatttagtaa cttctgtgtt

4741 aatactggat agcatgaatt ctgcattgag aaactgaata gctgtcataa aatgaaactt

4801 tctttctaaa gaaagatact cacatgagtt cttgaagaat agtcataact agattaagat

4861 ctgtgtttta gtttaatagt ttgaagtgcc tgtttgggat aatgataggt aatttagatg

4921 aatttagggg aaaaaaaagt tatctgcaga tatgttgagg gcccatctct ccccccacac

4981 ccccacagag ctaactgggt tacagtgttt tatccgaaag tttccaattc cactgtcttg

5041 tgttttcatg ttgaaaatac ttttgcattt ttcctttgag tgccaatttc ttactagtac

5101 tatttcttaa tgtaacatgt ttacctggaa tgtattttaa ctatttttgt atagtgtaaa

5161 ctgaaacatg cacattttgt acattgtgct ttcttttgtg ggacatatgc agtgtgatcc

5221 agttgttttc catcatttgg ttgcgctgac ctaggaatgt tggtcatatc aaacattaaa

5281 aatgaccact cttttaattg aaattaactt ttaaatgttt ataggagtat gtgctgtgaa

5341 gtgatctaaa atttgtaata tttttgtcat gaactgtact actcctaatt attgtaatgt

5401 aataaaaata gttacagtga caaaaaaaaa aaaaaa

Human KRAS, transcript variant b, comprising the LCS6 SNP (KRAS-variant), is encoded by the following mRNA sequence (SEQ ID NO: 12) (untranslated regions are bolded, LCS6 is underlined, SNP is capitalized):

1 ggccgcggcg gcggaggcag cagcggcggc ggcagtggcg gcggcgaagg tggcggcggc

61 tcggccagta ctcccggccc ccgccatttc ggactgggag cgagcgcggc gcaggcactg

121 aaggcggcgg cggggccaga ggctcagcgg ctcccaggtg cgggagagag gcctgctgaa

181 aatgactgaa tataaacttg tggtagttgg agctggtggc gtaggcaaga gtgccttgac 241 gatacagcta attcagaatc attttgtgga cgaatatgat ccaacaatag aggattccta 301 caggaagcaa gtagtaattg atggagaaac ctgtctcttg gatattctcg acacagcagg 361 tcaagaggag tacagtgcaa tgagggacca gtacatgagg actggggagg gctttctttg 421 tgtatttgcc ataaataata ctaaatcatt tgaagatatt caccattata gagaacaaat 481 taaaagagtt aaggactctg aagatgtacc tatggtccta gtaggaaata aatgtgattt -continued 541 gccttctaga acagtagaca caaaacaggc tcaggactta gcaagaagtt atggaattcc 601 ttttattgaa acatcagcaa agacaagaca gggtgttgat gatgccttct atacattagt 661 tcgagaaatt cgaaaacata aagaaaagat gagcaaagat ggtaaaaaga agaaaaagaa 721 gtcaaagaca aagtgtgtaa ttatgtaaat acaatttgta ctttttttctt aaggcatact

781 agtacaagtg gtaatttttg tacattacac taaattatta gcatttgttt tagcattacc

841 taattttttt cctgctccat gcagactgtt agcttttacc ttaaatgctt attttaaaat

901 gacagtggaa gttttttttt cctctaagtg ccagtattcc cagagttttg gtttttgaac

961 tagcaatgcc tgtgaaaaag aaactgaata cctaagattt ctgtcttggg gtttttggtg

1021 catgcagttg attacttctt atttttctta ccaattgtga atgttggtgt gaaacaaatt

1081 aatgaagctt ttgaatcatc cctattctgt gttttatcta gtcacataaa tggattaatt

1141 actaatttca gttgagacct tctaattggt ttttactgaa acattgaggg aacacaaatt

1201 tatgggcttc ctgatgatga ttcttctagg catcatgtcc tatagtttgt catccctgat

1261 gaatgtaaag ttacactgtt cacaaaggtt ttgtctcctt tccactgcta ttagtcatgg

1321 tcactctccc caaaatatta tatttttttct ataaaaagaa aaaaatggaa aaaaattaca

1381 aggcaatgga aactattata aggccatttc cttttcacat tagataaatt actataaaga

1441 ctcctaatag cttttcctgt taaggcagac ccagtatgaa atggggatta ttatagcaac

1501 cattttgggg ctatatttac atgctactaa atttttataa taattgaaaa gattttaaca

1561 agtataaaaa attctcatag gaattaaatg tagtctccct gtgtcagact gctctttcat

1621 agtataactt taaatctttt cttcaacttg agtctttgaa gatagtttta attctgcttg

1681 tgacattaaa agattatttg ggccagttat agcttattag gtgttgaaga gaccaaggtt

1741 gcaaggccag gccctgtgtg aacctttgag ctttcataga gagtttcaca gcatggactg

1801 tgtccccacg gtcatccagt gttgtcatgc attggttagt caaaatgggg agggactagg

1861 gcagtttgga tagctcaaca agatacaatc tcactctgtg gtggtcctgc tgacaaatca

1921 agagcattgc ttttgtttct taagaaaaca aactcttttt taaaaattac ttttaaatat

1981 taactcaaaa gttgagattt tggggtggtg gtgtgccaag acattaattt tttttttaaa

2041 caatgaagtg aaaaagtttt acaatctcta ggtttggcta gttctcttaa cactggttaa

2101 attaacattg cataaacact tttcaagtct gatccatatt taataatgct ttaaaataaa

2161 aataaaaaca atccttttga taaatttaaa atgttactta ttttaaaata aatgaagtga

2221 gatggcatgg tgaggtgaaa gtatcactgg actaggaaga aggtgactta ggttctagat

2281 aggtgtcttt taggactctg attttgagga catcacttac tatccatttc ttcatgttaa

2341 aagaagtcat ctcaaactct tagttttttt tttttacaac tatgtaattt atattccatt

2401 tacataagga tacacttatt tgtcaagctc agcacaatct gtaaattttt aacctatgtt

2461 acaccatctt cagtgccagt cttgggcaaa attgtgcaag aggtgaagtt tatatttgaa

2521 tatccattct cgttttagga ctcttcttcc atattagtgt catcttgcct ccctaccttc

2581 cacatgcccc atgacttgat gcagttttaa tacttgtaat tcccctaacc ataagattta

2641 ctgctgctgt ggatatctcc atgaagtttt cccactgagt cacatcagaa atgccctaca

2701 tcttatttcc tcagggctca agagaatctg acagatacca taaagggatt tgacctaatc

2761 actaattttc aggtggtggc tgatgctttg aacatctctt tgctgcccaa tccattagcg

2821 acagtaggat tttcaaacc tggtatgaat agacagaacc ctatccagtg gaaggagaat

2881 ttaataaaga tagtgctgaa agaattcctt aggtaatcta taactaggac tactcctggt

-continued 2941 aacagtaata cattccattg ttttagtaac cagaaatctt catgcaatga aaaatacttt 3001 aattcatgaa gcttactttt tttttttggt gtcagagtct cgctcttgtc acccaggctg 3061 gaatgcagtg gcgccatctc agctcactgc aacctccatc tcccaggttc aagcgattct 3121 cgtgcctcgg cctcctgagt agctgggatt acaggcgtgt gccactacac tcaactaatt 3181 tttgtatttt taggagagac ggggtttcac cctgttggcc aggctggtct cgaactcctg 3241 acctcaagtg atGcacccac cttggcctca taaacctgtt ttgcagaact catttattca 3301 gcaaatattt attgagtgcc taccagatgc cagtcaccgc acaaggcact gggtatatgg 3361 tatccccaaa caagagacat aatcccggtc cttaggtagt gctagtgtgg tctgtaatat 3421 cttactaagg cctttggtat acgacccaga gataacacga tgcgtatttt agttttgcaa 3481 agaaggggtt tggtctctgt gccagctcta taattgtttt gctacgattc cactgaaact 3541 cttcgatcaa gctactttat gtaaatcact tcattgtttt aaaggaataa acttgattat 3601 attgtttttt tatttggcat aactgtgatt cttttaggac aattactgta cacattaagg 3661 tgtatgtcag atattcatat tgacccaaat gtgtaatatt ccagttttct ctgcataagt 3721 aattaaaata tacttaaaaa ttaatagttt tatctgggta caaataaaca ggtgcctgaa 3781 ctagttcaca gacaaggaaa cttctatgta aaaatcacta tgatttctga attgctatgt 3841 gaaactacag atctttggaa cactgtttag gtagggtgtt aagacttaca cagtacctcg 3901 tttctacaca gagaaagaaa tggccatact tcaggaactg cagtgcttat gaggggatat 3961 ttaggcctct tgaatttttg atgtagatgg gcattttttt aaggtagtgg ttaattacct 4021 ttatgtgaac tttgaatggt ttaacaaaag atttgttttt gtagagattt taaaggggga 4081 gaattctaga aataaatgtt acctaattat tacagcctta aagacaaaaa tccttgttga 4141 agttttttta aaaaaagcta aattacatag acttaggcat taacatgttt gtggaagaat 4201 atagcagacg tatattgtat catttgagtg aatgttccca agtaggcatt ctaggctcta 4261 tttaactgag tcacactgca taggaattta gaacctaact tttataggtt atcaaaactg 4321 ttgtcaccat tgcacaattt tgtcctaata tatacataga aactttgtgg ggcatgttaa 4381 gttacagttt gcacaagttc atctcatttg tattccattg attttttttt tcttctaaac 4441 atttttttctt caaacagtat ataacttttt ttaggggatt tttttttaga cagcaaaaac 4501 tatctgaaga tttccatttg tcaaaaagta atgatttctt gataattgtg tagtaatgtt 4561 ttttagaacc cagcagttac cttaaagctg aatttatatt tagtaacttc tgtgttaata 4621 ctggatagca tgaattctgc attgagaaac tgaatagctg tcataaaatg aaactttctt 4681 tctaaagaaa gatactcaca tgagttcttg aagaatagtc ataactagat taagatctgt 4741 gttttagttt aatagtttga agtgcctgtt tgggataatg ataggtaatt tagatgaatt 4801 taggggaaaa aaaagttatc tgcagatatg ttgagggccc atctctcccc ccacaccccc 4861 acagagctaa ctgggttaca gtgttttatc cgaaagtttc caattccact gtcttgtgtt 4921 ttcatgttga aaatactttt gcatttttcc tttgagtgcc aatttcttac tagtactatt 4981 tcttaatgta acatgtttac ctggaatgta ttttaactat ttttgtatag tgtaaactga 5041 aacatgcaca ttttgtacat tgtgctttct tttgtgggac atatgcagtg tgatccagtt 5101 gttttccatc atttggttgc gctgacctag gaatgttggt catatcaaac attaaaaatg 5161 accactcttt taattgaaat taacttttaa atgtttatag gagtatgtgc tgtgaagtga 5221 tctaaaattt gtaatatttt tgtcatgaac tgtactactc ctaattattg taatgtaata 5281 aaaatagtta cagtgacaaa aaaaaaaaaa aa The present invention encompasses a SNP within the 3'UTR of KRAS. Specifically, this SNP is the result of a substitution of a G for a U at position 4 of SEQ ID NO: 6 of LCS6. This LCS6 SNP (KRAS-variant) comprises the sequence GAUGCACCCACCUUGGCCUCA (SNP bolded for emphasis) (SEQ ID NO: 13).

The KRAS-variant leads to altered KRAS expression by disrupting the miRNA regulation of a KRAS. The identification and characterization of the KRAS-variant is further described in International Application No. PCT/US08/65302 (WO 2008/151004), the contents of which are incorporated by reference in its entirety.

B. Methods of Prevention and Treatment of Cancer

The present inventors discovered that estrogen withdrawal in subjects with the KRAS-variant increases risk for both tumor development as well as aggressive breast cancer tumor biology, both in vivo and in vitro. Accordingly, the present invention relates to methods for preventing cancer in a KRAS-variant subject which include administering to the KRAS-variant subject an amount of estrogen effective to reduce the risk of developing cancer. For example, the method may include administering to a KRAS-variant subject a tapering dose of estrogen, starting with the patient's pre-oophorectomy baseline estrogen levels, or pre-chemotherapy estrogen levels, which can be calculated. Estrogen may be administered as any HRT or birth control formulation known in the art. In certain embodiments, the dose of estrogen administered starts at 0.1 mg/kg estrogen, and the dosage is decreased over time.

In another aspect, the invention relates to methods for treating cancer in a KRAS-variant subject, which include reducing estrogen activity in the KRAS-variant subject to reduce the risk of aggressive tumor growth. In certain embodiments, estrogen exposure is gradually decreased by antagonizing estrogen function, for example, by administering an estrogen antagonist or an estrogen receptor antagonist. In certain embodiments, the estrogen receptor antagonist is tamoxifen. The tamoxifen may be administered at 10 or 20 mg twice a day for three months or at 10 or 20 mg once daily for three months. In certain embodiments, the estrogen receptor antagonist is a selective estrogen receptor modulator (SERM) or selective estrogen receptor down-regulator (SERD). In certain embodiments, the SERM is clomifene, femarelle, ormeloxifene, raloxifene, toremifene, lasofoxifene, ospemifene, afimoxifene, arzoxifene or bazedoxifene. In certain embodiments, the SERD is fulvestrant (Faslodex®). Any dosage of the estrogen antagonist or estrogen receptor antagonist known in the art may be used. Administration of the estrogen antagonist or estrogen receptor antagonist may continue for three months, six months, one year, two years, three years, four years, five years, or indefinitely.

Gradually decreasing estrogen function can include reducing the amount of HRT or estrogen administered over a period of, e.g., one week, two weeks, one to six weeks, one month, two months, one to six months, two to six months, six months to a year, one year, two years, three years, four years and five years. The amount of HRT or estrogen administered can be reduced to zero, or to a low, maintenance dosage. Reduction of HRT or estrogen can occur by reducing HRT or estrogen by, e.g., 1%, 2%, 5%, 10%, 15%, 30%, or 50%, over a period of, e.g., one week, two weeks, one to six weeks, one month, two months, one to six months, two to six months, six months to a year, one year, two years, three years, four years and five years.

Gradually decreasing estrogen function can include increasing dosage of an estrogen antagonist or an estrogen receptor antagonist over a period of, e.g., one week, two weeks, one to six weeks, one month, two months, one to six months, two to six months, six months to a year, one year, two years, three years, four years and five years. Increasing dosage of an estrogen antagonist or an estrogen receptor antagonist can occur by increasing the dosage of estrogen antagonist or an estrogen receptor antagonist by, e.g., 50%, 100%, 200%, 500%, or 1000% over a period of, e.g., one week, two weeks, one to six weeks, one month, two months, one to six months, two to six months, six months to a year, one year, two years, three years, four years and five years.

C. Agents

1. Estrogen, Estrogen Analogs, Estrogen Agonists

Forms of estrogen, estrogen analogs and estrogen agonists suitable for use with the present invention include estradiol, estradiol acetate, ethinyl estradiol, mestranol, conjugated synthetic estrogens (e.g., Enjuvia®, which contains sodium delta-8,9-dehydroestrone sulfate, sodium estrone sulfate, sodium equilin sulfate, sodium 7-alpha-dihydroequilin sulfate, sodium 17-alpha-estradiol sulfate, sodium 17-beta-dihydroequilin sulfate, sodium 17-alpha-dihydroequilenin sulfate, sodium 17-beta-dihydroequilenin sulfate, sodium equilenin sulfate, and sodium 17-beta-estradiol sulfate.), and conjugated equine estrogens (e.g., Premarin®). Estrogen may be administered by any means known in the art, including orally, transdermally, vaginally. Estrogen dosages suitable for use with the present invention include, for example, between about 0.01 to about 0.1 mg/day. In certain embodiments, 15 μg, 20 μg, 30 μg, or 50 μg estrogen (e.g., ethinyl estradiol) is administered per day for a given time period (e.g., 21 days), and then administration is repeated immediately, or after a week of no administration.

2. Agents that Antagonize Estrogen Function

One class of agents that antagonize estrogen function suitable for use in the present invention prevents hormones from attaching to cancer cells, e.g., Tamoxifen. Tamoxifen is a selective estrogen receptor modulator (SERM). SERMs act by blocking any estrogen present in the body from attaching to the estrogen receptor on the cancer cells, slowing the growth of tumors and killing tumor cells. In certain embodiments, the SERM is clomifene, femarelle, ormeloxifene, raloxifene, toremifene, lasofoxifene, ospemifene, afimoxifene, arzoxifene or bazedoxifene. In certain embodiments, a selective estrogen receptor down-regulator (SERD) is used. In certain embodiments, the SERD is fulvestrant (Faslodex®). Tamoxifen can be used in both pre- and postmenopausal women.

Another class of agents that antagonize estrogen function suitable for use in the present invention arrest estrogen production after menopause. For instance, aromatase inhibitors block the action of an enzyme that converts androgens into estrogen. Specifically, aromatase inhibitors are effective only in postmenopausal women, and include commonly known drugs, such as, anastrozole (Arimidex), letrozole (Femara) and exemestane (Aromasin).

D. Formulations

Pharmaceutical compositions of the disclosure (e.g., estrogen or agents that antagonize estrogen function) may be administered by various means, depending on their intended use, as is well known in the art. For example, if compositions of the disclosure are to be administered orally, they may be formulated as tablets, capsules, granules, powders or syrups. Alternatively, formulations disclosed herein may be administered parenterally as injections (intravenous, intramuscular or subcutaneous), drop infusion preparations or suppositories. For application by the ophthalmic mucous membrane route, the compositions disclosed herein may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. The disclosed excipients may serve more than one function. For example, fillers or binders may also be disintegrants, glidants, anti-adherents, lubricants, sweeteners and the like.

In formulations of the disclosure, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal (e.g., by inhalation using a dry powder formulation or a nebulized formulation), topical (including buccal and sublingual), pulmonary (including aerosol administration), rectal, vaginal, aerosol and/or parenteral (e.g., by injection, for example, intravenous or subcutaneous injection) administration. The formulations may conveniently be presented in unit dosage form and may be prepared by any methods well known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the disclosure may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, dextrose, lactose, sucrose, glucose, mannitol, and/or silicic acid; (2) binders, such as, for example, celluloses (e.g., microcrystalline cellulose, methyl cellulose, hydroxypropylmethyl cellulose (HPMC) and carboxymethylcellulose), alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like. The disclosed excipients may serve more than one function. For example, fillers or binders may also be disintegrants, glidants, anti-adherents, lubricants, sweeteners and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. The disclosed excipients may serve more than one function. For example, fillers or binders may also be disintegrants, glidants, anti-adherents, lubricants, sweeteners and the like.

It will be appreciated that a disclosed composition may include lyophilized or freeze dried compounds disclosed herein. For example, disclosed herein are compositions that disclosed compounds crystalline and/or amorphous powder forms. Such forms may be reconstituted for use as e.g., an aqueous composition.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, and patches. The active component may be mixed under sterile conditions with a pharmaceutically acceptable carrier, and with any preservatives, buffers, or propellants that may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, fillers or binders can also be disintegrants, glidants, anti-adherents, lubricants, sweeteners and the like.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. For example, provided herein is an aqueous composition that includes a disclosed compound, and may further include for example, dextrose (e.g., about 1 to about 10 weight percent dextrose, or about 5 weight percent dextrose in water (D5W).

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

It will be appreciated that contemplated formulations, such as oral formulations (e.g. a pill or tablet), may be formulated as controlled release formulation, e.g., an immediate release formulation, a delayed release formulation, or a combination thereof.

In certain embodiments, the subject compounds may be formulated as a tablet, pill, capsule or other appropriate ingestible formulation (collectively hereinafter "tablet"). In certain embodiments, a therapeutic dose may be provided in 10 tablets or fewer. In another example, a therapeutic dose is provided in 50, 40, 30, 20, 15, 10, 5 or 3 tablets.

E. Methods of Predicting Risk

The invention also features methods of predicting an increased risk of developing a second, independent breast cancer in a subject. The method includes detecting a single nucleotide polymorphism (SNP) at position 4 of the let-7 complementary site 6 of KRAS in a patient sample wherein the presence of said SNP indicates an increased risk of developing a second, independent cancer in said subject. Specifically the mutation that is detected is a SNP at position 4 of LCS6 of KRAS of which results in a uracil (U) or thymine (T) to guanine (G) conversion. In certain embodiments, the second, independent cancer is breast cancer. In certain embodiments, the subject is a breast cancer patient.

Identification of the mutation indicates an increases risk of developing synchronous and asynchronous second breast cancer. "Risk" in the context of the present invention, relates to the probability that an event will occur over a specific time period, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a primary tumor to a metastatic tumor or to one at risk of developing a metastatic, or from at risk of a primary metastatic event to a secondary metastatic event or from at risk of a developing a primary tumor of one type to developing a one or more primary tumors of a different type. Risk evaluation can also comprise prediction of future clinical parameters, traditional laboratory risk factor values, or other indices of cancer, either in absolute or relative terms in reference to a previously measured population.

An "increased risk" is meant to describe an increased probability that an individual who carries the KRAS-variant develops synchronous or asynchronous second breast cancer, compared to an individual who does not carry KRAS-variant. In certain embodiments, a KRAS-variant carrier is 1.5×, 2×, 2.5×, 3×, 3.5×, 4×, 4.5×, 5×, 5.5×, 6×, 6.5×, 7×, 7.5×, 8×, 8.5×, 9×, 9.5×, 10×, 20×, 30×, 40×, 50×, 60×, 70×, 80×, 90×, or 100× more likely to develop a synchronous or asynchronous second breast cancer than an individual who does not carry the KRAS-variant.

A subject is preferably a mammal. The mammal can be a human, non-human primate, mouse, rat, dog, cat, horse, or cow, but are not limited to these examples. A subject can be male or female.

The biological sample can be any tissue or fluid that contains nucleic acids. Various embodiments include paraffin imbedded tissue, frozen tissue, surgical fine needle aspirations, and cells of the breast, endometrium, ovaries, uterus, or cervix. Other embodiments include fluid samples such peripheral blood lymphocytes, lymph fluid, ascites, serous fluid, sputum, and stool or urinary specimens such as bladder washing and urine.

Linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium". In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD.

For screening individuals for genetic disorders (e.g. prognostic or risk) purposes, if a particular SNP site is found to be useful for screening a disorder, then the skilled artisan would recognize that other SNP sites which are in LD with this SNP site would also be useful for screening the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome.

For screening applications, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., disease) that is influenced by the causative SNP(s). Thus, polymorphic markers that are in LD with causative polymorphisms are useful as markers, and are particularly useful when the actual causative polymorphism (s) is/are unknown.

Linkage disequilibrium in the human genome is reviewed in: Wall et al. (2003) Nat Rev Genet. 4(8):587-97; Gamer et al. (2003) Genet Epidemiol. 24 (1):57-67; Ardlie et al. (2002) Nat Rev Genet. 3(4):299-309 (erratum in (2002) Nat Rev Genet 3(7):566); and Remm et al. (2002) Curr Opin Chem Biol. 6(1):24-30.

The screening techniques of the present invention may employ a variety of methodologies to determine whether a test subject has a SNP or a SNP pattern associated with an increased or decreased risk of developing a detectable trait or whether the individual suffers from a detectable trait as a result of a particular polymorphism/mutation, including, for example, methods which enable the analysis of individual chromosomes for haplotyping, family studies, single sperm DNA analysis, or somatic hybrids. The trait analyzed using the diagnostics of the invention may be any detectable trait that is commonly observed in pathologies and disorders.

F. SNP Genotyping Methods

The process of determining which specific nucleotide (i.e., allele) is present at each of one or more SNP positions, such as a SNP position in a nucleic acid molecule disclosed in SEQ ID NO: 11, 12 or 13, is referred to as SNP genotyping. The present invention provides methods of SNP genotyping, such as for use in screening for a variety of disorders, or determining predisposition thereto, or determining responsiveness to a form of treatment, or prognosis, or in genome mapping or SNP association analysis, etc.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al. (2003) Pharmacogenomics J. 3(2):77-96; Kwok et al. (2003) Curr Issues Mol. Biol. 5(2):43-60; Shi (2002) Am J Pharmacogenomics 2(3):197-205; and Kwok (2001) Annu Rev Genomics Hum Genet 2:235-58. Exemplary techniques for high-throughput SNP genotyping are described in Marnellos (2003) Curr Opin Drug Discov Devel. 6(3):317-21. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA duplexes (Myers et al. (1985) Science 230:1242; Cotton et al. (1988) PNAS 85:4397; and Saleeba et al. (1992) Meth. Enzymol. 217:286-295), comparison of the electrophoretic mobility of variant and wild type nucleic acid molecules (Orita et al. (1989) Pnas 86:2766; Cotton et al. (1993) Mutat. Res. 285:125-144; and Hayashi et al. (1992) Genet. Anal. Tech. Appl. 9:73-79), and assaying the movement of polymorphic or wild-type fragments in polyacrylamide gels containing a gradient of denaturant using denaturing gradient gel electrophoresis (DGGE) (Myers et al. (1985), Nature 313:495). Sequence variations at specific locations can also be assessed by nuclease protection assays such as RNase and SI protection or chemical cleavage methods.

In a preferred embodiment, SNP genotyping is performed using the TaqMan assay, which is also known as the 5' nuclease assay (U.S. Pat. Nos. 5,210,015 and 5,538,848). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the SNPs of the present invention are useful in prognostic assays for a variety of disorders including cancer, and can be readily incorporated into a kit format. The present invention also includes modifications of the Taqman assay well known in the art such as the use of Molecular Beacon probes (U.S. Pat. Nos. 5,118,801 and 5,312,728) and other variant formats (U.S. Pat. Nos. 5,866,336 and 6,117,635).

The identity of polymorphisms may also be determined using a mismatch detection technique, including but not limited to the RNase protection method using riboprobes (Winter et al. (1985) Pnas 82:7575; Meyers et al. (1985) *Science* 230:1242) and proteins which recognize nucleotide mismatches, such as the *E. coli* mutS protein (Modrich (1991) *Ann. Rev. Genet.* 25:229-253). Alternatively, variant alleles can be identified by single strand conformation polymorphism (SSCP) analysis (Orita et al. (1989) *Genomics* 5:874-879; Humphries et al., in Molecular Diagnosis of Genetic Diseases, R. Elles, ed., pp. 321-340, 1996) or denaturing gradient gel electrophoresis (DGGE) (Wartell et al. (1990) *Nucl. Acids Res.* 18:2699-2706; Sheffield et al. (1989) *PNAS* 86:232-236).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruano et al. (1989) Nucl. Acids Res. 17:8392; Ruano et al. (1991) Nucl. Acids Res. 19, 6877-6882; WO 93/22456; Turki et al. (1995) J Clin. Invest. 95:1635-1641). In addition, multiple polymorphic sites may be investigated by simultaneously amplifying multiple regions of the nucleic acid using sets of allele-specific primers as described in Wallace et al. (WO89/10414).

Another preferred method for genotyping the SNPs of the present invention is the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of OLA: U.S. Pat. Nos. 6,027,889, 6,268,148, 5,494,810, 5,830,711, and 6,054,564 describe OLA strategies for performing SNP detection; WO 97/31256 and WO 00/56927 describe OLA strategies for performing SNP detection using universal arrays, wherein a zipcode sequence can be introduced into one of the hybridization probes, and the resulting product, or amplified product, hybridized to a universal zip code array; U.S. application US01/17329 (and Ser. No. 09/584,905) describes OLA (or LDR) followed by PCR, wherein zipcodes are incorporated into OLA probes, and amplified PCR products are determined by electrophoretic or universal zipcode array readout; U.S. application 60/427,818, 60/445,636, and 60/445,494 describe SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization—Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

Typically, the primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position. For further information regarding the use of primer extension assays in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry", Rapid Commun Mass Spectrom. 2003; 17 (11):1195-202.

The following references provide further information describing mass spectrometry-based methods for SNP genotyping: Bocker (2003) Bioinformatics 19 Suppl 1:144-153; Storm et al. (2003) Methods Mol. Biol. 212:241-62; Jurinke et al. (2002) Adv Biochem Eng Biotechnol. 77:57-74; and Jurinke et al. (2002) Methods Mol. Biol. 187:179-92.

SNPs can also be scored by direct DNA sequencing. A variety of automated sequencing procedures can be utilized ((1995) Biotechniques 19:448), including sequencing by mass spectrometry (see, e.g., PCT International Publication No. WO94/16101; Cohen et al. (1996) Adv. Chromatogr. 36:127-162; and Griffin et al. (1993) Appl. Biochem. Biotechnol. 38:147-159). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

Other methods that can be used to genotype the SNPs of the present invention include single-strand conformational polymorphism (SSCP), and denaturing gradient gel electrophoresis (DGGE) (Myers et al. (1985) Nature 313:495). SSCP identifies base differences by alteration in electrophoretic migration of single stranded PCR products, as described in Orita et al., Proc. Nat. Acad. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel (Erlich, ed., PCR Technology, Principles and Applications for DNA Amplification, W. H. Freeman and Co, New York, 1992, Chapter 7).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis SNP genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

EXAMPLES

Example 1

Summary:

Women with breast cancer (BC) were recruited to join this study, asked to complete a questionnaire on life hormonal exposures, and required to supply a DNA sample for KRAS-variant testing (n=1712). A group of KRAS-variant unaffected (cancer free) female controls (n=80) were collected to compare with KRAS-variant BC patients (n=286). The association of life hormonal exposures with BC was evaluated, as was tumor biology in post-menopausal women with and without a history of hormone replacement therapy. Isogenic normal breast epithelial cell lines with or without the KRAS-variant were used to confirm the impact of estrogen withdrawal on transformation in vitro. The association of the KRAS-variant with second primary breast cancer development was assessed, as were characteristics of presentation.

Compared to non-variant BC patients, KRAS-variant BC patients went through menopause at a significantly younger age (p=0.048), and were more likely to be on hormone replacement therapy (HRT) when diagnosed with BC (p=0.032). For women with the KRAS-variant, a history of discontinuation of hormone replacement therapy (HRT) was significantly associated with triple negative breast cancer tumor biology and higher tumor grade. Compared to KRAS-variant cancer free controls, KRAS-variant BC patients were younger at menopause (p=0.035), had fewer live births (p<0.001), were older at the time of their first birth (p=0.014), were more likely to have used OCPs (p=0.041), and had a lower body mass index (BMI) (p<0.001). Isogenic breast cell lines with the KRAS-variant exhibited transformation with acute estrogen withdrawal, consistent with the clinical findings. Most strikingly, homozygous KRAS-variant patients (GG) had over an 11 fold increased risk of developing a second primary breast cancer compared to non-variant patients (45.39% vs 6.78%, OR 11.44 [3.42-37.87], p<0.001). As a group (TG+GG), KRAS-variant BC patients were over twice as likely to be diagnosed with a second, independent breast cancer than non-variant patients (12.93% vs 6.78%; OR 2.04 [1.36-3.06], p<0.001). These findings were significant controlling for lobular histology, length of follow-up and type of surgery.

Methods

Study Groups:

A cohort of breast cancer patients were invited to join a study through the Susan Love foundation, called "The KRAS-variant and hormones" (http://www.armyofwomen.org/current/view?grant_id=438). 1906 women responded to the invitation and completed questionnaires regarding age at diagnosis; anthropomorphic measurements including weight and height; reproductive history including parity, age at first birth, use of contraceptives and hormone replacement therapy; and personal and familial cancer history. Participants signed a consent approved through the Yale University Human Investigation Committee (HIC), and were mailed a cheek swab or saliva kit (Oragene) for DNA testing, and requested to supply pathology reports for their BC(s). Pathology reports were used in all cases of second primary breast cancers, where synchronous second primary breast cancers were either in the contralateral breast, or if in the same breast were classified as multi-centric on the pathology reports, with different pathologies. Metachronous breast cancer was of different pathology if in the same breast and classified as a new primary, or in the contralateral breast.

Control samples were provided by the Human Genetics Sample bank at the Ohio State University Medical Center (OSUMC). All controls were women who had the KRAS-variant but were unaffected by cancer at the time of testing, n=80. The Columbus Area Controls Sample Bank is a collection of control samples for use in human genetics research that includes both donors' anonymized biological specimens and linked phenotypic data. The data and samples are collected under the protocol "Collection and Storage of Controls for Genetics Research Studies", which is approved by the Biomedical Sciences Institutional Review Board at OSUMC. Recruitment takes place in OSUMC primary care and internal medicine clinics. If individuals agree to participate, they provide written informed consent, complete a questionnaire that includes demographic, medical and family history information, and donate a blood sample, which is used for genomic DNA extraction and the establishment of an EBV-transformed lymphoblastoid cell culture, cell pellet in Trizol, and plasma.

KRAS-Variant Testing:

For all participants, DNA was extracted from buccal swabs or saliva according to the manufacturer's protocol (Oragene). Coded patient samples were genotyped for the KRAS-variant using a Taqman-based assay, in the MiraDx CLIA certified laboratory, as previously described (Chin, supra).

Isogenic Cell Line Creation:

MCF10a cells are an immortalized, non-transformed mammary epithelial cell line derived from human fibrocystic mammary tissue. These cells have several characteristics of normal human breast epithelium, including lack of tumorigenicity in nude mice and lack of anchorage independent growth (Soule et al. (1990) Cancer Res. 50:6075-6086). The karyotype of this cell line is near diploid with minimal rearrangement, and they are dependent on exogenous growth factors and hormones for proliferation and survival. They do not express Estrogen Receptor α (ERα). Furthermore, MCF10a cells can form three-dimensional structures in a reconstituted basement membrane resulting in formation of polarized, growth-arrested acini-like spheroids, which are similar to glandular architecture of epithelium in vivo. (Debnath et al. (2003) Methods 30:256-268).

Isogenic MCF10A lines were generated with and without the KRAS-variant using the CompoZr™ custom designed zinc-finger nuclease (ZFN) targeted genome editing technology (Sigma-Aldrich, per manufacturer's instructions) (Urnov et al. (2005) NATURE 435(7042):646-51). A ZFN pair was designed and constructed to specifically target the KRAS 3'UTR. The donor construct containing the homology arms on either side of the KRAS-variant was generated by PCR amplifying a 2087 base pair region containing the KRAS-variant from genomic DNA with forward primer 5' AGGACTCTGATTTTGAGGACATC 3' (SEQ ID NO: 14) and reverse primer 5' AACATGCCCCACAAAGTTTC 3' (SEQ ID NO: 15) and cloning into the pGEM-T (Promega) cloning vector. The ZFN plasmids (500 ng) and the donor plasmid (2 μg) were transfected into $2\times10^5$ MCF10A cells by nucleofection, program T-024, according to manufacturer's instructions (Amaxa), in media containing 100 μM chloroquine. The media was changed after 4 hrs and the cells were incubated overnight and re-seeded as single cells into 24-well plates. After passage and DNA collection, clones were assessed for the presence of the KRAS-variant using an allele-specific primer and a PCR-based TaqMan assay. Secondary validation was carried out by allele-specific sequencing of TOPO TA® cloned, PCR amplified genomic DNA using forward primer 5' AAGGCATACTAGTACAAGTG- GTAATTT 3' (SEQ ID NO: 16) and reverse primer 5' TAGGAGTAGTACAGTTCATGACAAAAA 3' (SEQ ID NO: 17), which hybridize to the KRAS locus outside of the region corresponding to the donor plasmid recombination site. In addition, two positive clones were authenticated using bi-allelic short tandem repeat (STR) analysis at 16 different genomic loci, yielding 32 diagnostic markers for confirmation. (Genetica DNA Laboratories, Inc.) STR analysis confirmed that the MCF10A$^{RAS\text{-}variant-/-}$ (Parental, WT) and the two MCF10A$^{KRAS\text{-}variant+/-}$ (MT) cell lines were (a) identical to the ATCCs STR profile and (b) identical to each other, except for the presence or absence of the KRAS-variant.

Real-Time PCR for Epithelial and Mesenchymal Markers:

Total RNA was extracted from 2 independent preparations of cells using TRIzol using standard procedures. cDNA libraries were generated (in duplicate) from 1 μg of total RNA using the iScript cDNA Library Synthesis Kit (Bio-Rad). mRNA was analyzed (in triplicate) by qPCR using iQ SYBR Green SuperMix (BioRad) in reactions containing gene specific primers (listed below). Reactions were amplified in a HT7900 (Applied Biosystems) for 10 minutes at 95° C. followed by 40 cycles at 95° C. for 15 seconds and 60° for 1 minute. mRNA expression was normalized to Beta-Actin and relative expression was calculated using the delta-delta Ct method. Primers were designed to span exon-intron-exon junctions and produced amplicons of approximately 500 bp. Primers were synthesized at the Yale Keck Oligonucleotide Synthesis facility.

Western Blotting:

1.5×106 cells in, log growth phase, were washed with ice cold PBS pH 7.4 and lysed with 0.5 ml of SDS Sample buffer (BioRad). Whole cell lysates were boiled at 95° C. for 5 minutes. Increasing amount of whole cell lysate (2, 4 and 8 ul) were loaded on a 4-20% gradient gel (BioRad) for quantification. Proteins were transferred to PVDF membrane and blotted for using the following antibodies:

| Protein | Vendor | Catalog Number |
|---|---|---|
| GAPD | Abcam | [6C5] (ab8245) |
| Vimentin | Abcam | [V9] (ab8069) |
| Fibronectin | Abcam | (ab2413) |
| Occludin | Abcam | [EPR8208] (ab167161) |
| E-Cadherin | Abcam | (ab15148) |
| N-Cadherin | Abcam | (ab18203) |
| Sheep Anti-Mouse IgG HRP | GE Healthcare Life Sciences | (NA931) |
| Donkey Anti-Rabbit IgG HRP | GE Healthcare Life Sciences | (NA934) |

Protein was visualized using ECL Western Blotting Detection Reagent (GE Healthcare Life Sciences).

Cell Line and Anchorage Independent Growth Assays:

MCF10A (WT) and (MT) cells were cultured in regular DMEM/F12 medium (Invitrogen) as per the Brugge lab protocol (Debnath et al. (2003) METHODS 30:256-268). 3D Matrigel growth experiments were carried out as per Debnath et al. (Id.) Briefly, eight-well slides (Thermo Scientific) were coated with 40 μl of Growth Factor Reduced (GFR) Matrigel™ (BD Bioscience) per well and left to solidify for 20 minutes at 37° C. in a humidified CO2 incubator. Cell suspension (12,500 cells/ml) in regular growth media with 20 ng/ml of EGF was prepared. 2% of GFR Matrigel™ was added to the cell suspension. 400 μl of Matrigel™ and cell suspension mixture (total 5000 cells) was added to each well of a Matrigel™ precoated chamber slide. Media containing 20 ng/ml EGF was replaced every 4-days. Cells were photographed on day 15 at 10× magnification.

Anchorage independent growth was assessed as described previously (Sweasy et al. (2005) PNAS 102:14350-5). After thawing and growing cells until confluence in EGF supplemented media (20 ng/ml), cells were plated into conditions of study for two passages. For estrogen depletion experiments phenol red free DMEM/F12 medium (Invitrogen) and 5% charcoal-stripped horse serum (Thermo Fisher) were used, and Tamoxifen or estrogen was added to a final concentration of 1 μM after the first passage, as appropriate. To plate, 100 μl of MCF10A (WT) or (MT) cells at a density of 400,000 cells/ml were mixed with 2 ml of media for the condition under study containing 2 ml 0.7% noble agar (USB). 1 ml of the cell mixture was added to 1 ml of 1.0% noble agar in a well of a 6-well dish. Cells were fed twice weekly by layering on a 50:50 mixture of media with 0.7% agar for 2 weeks, followed by only media for two-three additional weeks. The number of colonies present in each of ten microscope fields per well from a total of 3 wells per experiment was counted to evaluate transformation and is reported as an average of the 2 separate MT lines.

MicroRNA Microarray Analysis:

Total RNA was extracted from cells using Trizol as standard. MicroRNA cDNA libraries were generated from total RNA (1 ug) using Megaplex RT Primers (Human Pool A, Applied Biosystems). MicroRNA expression was analyzed using a TaqMan Array Human MicroRNA Card A v2.0 (Applied Biosystems). Reactions were cycled in a HT7900 (Applied Biosystems) for 10 minutes at 95° C. followed by 40 cycles at 95° C. for 15 seconds and 60° C. for 1 minute. miRNAs that had a Ct value of >35.0000 were excluded from further analysis. Relative expression was calculated using the delta-delta Ct method.

Data Analysis:

Data was analyzed using the R environment for statistical computing and graphics. Continuous data was assessed for normality using Shapiro-Wilk test and parametric or non-parametric tests applied as appropriate. Student t tests were used to compare continuous variables that were normally distributed and Mann Whitney U test for non-normally distributed data. Categorical data was analyzed using 2×2 contingency tables (chi-square). In order to assess association between the likelihood of being diagnosed with a second primary breast cancer and KRAS variants, we used logistic regression and quantified differential risk through odds ratios (OR). A similar analysis was replicated to associate the time from primary diagnosis to diagnosis with a second primary breast cancer through the Cox proportional hazard model. Differential timing of second primary cancers was compared through hazard ratios (HR). In both modelling frameworks, when adjusting for potential confounders, we selected order and scope of interaction effects through the Bayesian Information Criterion (BIC). In the Cox proportional hazard model, the assumption of proportionality was assessed both visually by inspection of Kaplan-Meier survival curves and formally, through the analysis of Schoenfeld residuals (p. val>0.10).

Results

KRAS-Variant Versus Non-Variant BC Patients

Of the 1712 patients who supplied DNA samples, 17.4% (n=298) had the KRAS-variant, and 70 (4.0%) had other known genetic mutations associated with increased breast cancer risk, including BRCA1, BRCA2 and PTEN. In the 1642 women without other mutations, 286 (17.42%) had the KRAS-variant, and 1356 (82.58%) did not. Association of self-reported estrogen exposures in these BC patients were evaluated to determine if there were differences for BC patients with versus those without the KRAS-variant.

KRAS-variant BC patients in this cohort had a similar age of diagnosis (51 years vs 50 years, NS), interval since diagnosis and enrollment (6 years, NS), proportion premenopausal (50% vs. 55%), pregnancy rate, birth rate, oral contraceptive (OCP) use, age of menopause, HRT use and Body Mass Index (BMI), as non-variant BC patients. However, by univariate analysis, KRAS-variant BC patients were significantly more likely to have had an oophorectomy before their BC diagnosis (15.5% vs 10.7%, p=0.024) and to be on HRT when diagnosed with breast cancer (66.3% versus 54.4%, p=0.034) than non-variant BC patients (Table 1). By multivariate analysis, KRAS-variant BC patients continued to be significantly more likely to have a history of ovarian removal (oophorectomy) pre-diagnosis (OR=1.42, CI 1.03-1.42, p=0.033) (Table 1). In addition, although KRAS-variant patients were not significantly more likely to have a family history of breast or ovarian cancer than non-variant BC patients (62.66% vs 64.01%, NS), they were significantly more likely to have a family history of an individual with multiple primary cancers than non-variant BC patients (4.98% vs 0.92%, p<0.0001).

TABLE 1

KRAS-variant breast cancer versus non-variant breast cancer patients.

|  |  | Non-variant 1356 | KRAS-variant 286 | P | Test |
|---|---|---|---|---|---|
| Age at diagnosis |  | 50 (24-77) | 51 (24-72) | 0.576 | Mann Whitney U |
| Oophorectomy before diagnosis |  | 145 (10.7%) | 44 (15.4%) | 0.024 | $X^2$ |
| Interval between diagnosis and enrollment |  | 6 (0-40) | 6 (0-35) | 0.142 | Mann Whitney U |
| Age at menopause |  | 49 (25-59) | 48 (27-57) | 0.07 | Mann Whitney U |
| Menopausal status[1] | Pre | 748 (55%) | 142 (50%) | 0.089 | $X^2$ |
|  | Post | 608 (45%) | 144 (50%) |  |  |
| HRT use[2] | Yes | 401 (67%) | 104 (73%) | 0.192 | $X^2$ |
|  | No | 195 (33%) | 39 (27%) |  |  |
| On HRT at diagnosis[3] | Yes | 217 (54%) | 68 (66%) | 0.034 | $X^2$ |
|  | No | 182 (46%) | 35 (34%) |  |  |
| Duration of HRT[3] |  | 60 (2-384) | 66 (1-444) | 0.586 | Mann Whitney U |
| Pregnancy | Nulliparous | 304 | 62 | 0.801 | $X^2$ |
|  | ≥1 pregnancy | 1046 | 222 |  |  |
|  | Number of pregnancies[4] | 2 (1-11) | 2 (1-9) | 0.614 | Mann Whitney U |
|  | Number of live births[4] | 2 (0-7) | 2 (0-5) | 0.218 | Mann Whitney U |
|  | Age at first birth | 27 (15-45) | 26 (16-39) | 0.085 | Mann Whitney U |
| OCP | Yes | 1155 | 251 | 0.280 | $X^2$ |
|  | No | 199 | 35 |  |  |
|  | Duration (yrs) | 7.75 (0.08-35) | 7.5 (0.1-40) | 0.971 | Mann Whitney U |
| BMI |  | 24.38 (15.73-64.36) | 24.27 (18.01-46.98) | 0.824 | Mann Whitney U |

[1] At diagnosis, cases; at sampling, controls
[2] For post-menopausal women only
[3] For women on HRT only
[4] Excluding nulliparous women Women with breast cancer with the KRAS-variant were younger at the age of menopause, and were more likely to be on hormone replacement therapy (HRT) at the time of diagnosis, compared to non-variant breast cancer patients.

TABLE 2

KRAS-variant BC cases compared to non-variant BC cases.
BC Patient Characteristics with versus without the KRAS-Variant

|  | OR (95% C.I.) [p. val] |
|---|---|
| Baseline | Prob = 15.88% |
| Lobular | 0.82 (0.53, 1.26) [0.365] |

TABLE 2-continued

KRAS-variant BC cases compared to non-variant BC cases.
BC Patient Characteristics with versus without the KRAS-Variant

|  | OR (95% C.I.) [p. val] |
|---|---|
| ER positive | 0.76 (0.52, 1.11) [0.154] |
| Ovaries removed | 1.42 (1.03, 1.96) [0.033] |
| BMI | 0.98 (0.96, 1.01) [0.277] |
| BCP | 1.23 (0.78, 1.94) [0.364] |
| Personal Cancer History | 0.80 (0.54, 1.20) [0.278] |
| Age at Diagnosis | 1.00 (0.98, 1.03) [0.705] |
| Menopause at Diagnosis | 1.27 (0.83, 1.96) [0.266] |
| Ever pregnant | 0.93 (0.65, 1.32) [0.686] |

By a logistic regression model, with predictors included in the model assuming a linear additive structure, BC patients with the KRAS-variant were more likely to have had an oophorectomy compared to non-variant breast cancer patients The Association of HRT Breast Cancer Subtype and Grade Because of the significant association of HRT use in KRAS-variant BC patients in the cohort, and a prior report of altered tumor biology and higher grade for KRAS-variant HRT users (Cerne, supra), association of HRT use and histologic BC tumor subtype (ER/PR+, HER2+, or ER/PR/HER2− [triple negative]) and grade was evaluated. Postmenopausally diagnosed BC patients were divided into three HRT use groups based on their HRT use at the time of their diagnosis. These groups comprised "never users," "current users" (women on HRT at the time of the BC diagnosis), or "past HRT users" (women with a history of HRT use preceding their BC diagnosis by at least 6 months). Histologic BC tumor subtypes for KRAS-variant (n=133) were then compared to non-variant BC patients (n=612) for those with complete histologic tumor information.

Overall, there was no difference in tumor grade between KRAS-variant BC versus non-variant patients, but triple negative breast cancer (TNBC) tumor subtype was significantly more common in women with the KRAS-variant (p=0.029). The correlation between HRT use and histologic BC tumor subtype and grade was then studied. For non-variant BC patients, there were no differences in the proportion of women with each tumor subtype between the never, current or past HRT user groups. However, there was a trend for current or past HRT users to have lower grade breast tumors than never users in agreement with prior reports (Calle, supra), but this difference was not statistically significant. In KRAS-variant BC patients, there were no statistically significant differences in tumor subtype or grade between KRAS-variant never and current HRT users. However, past HRT users were significantly more likely to have TNBC than KRAS-variant never or current HRT BC patients (35.5% [n=11/31] versus 6.6% [n=6/91], p<0.0001). In addition, compared to non-variant past HRT users, KRAS-variant past HRT users were significantly more likely to have TNBC (35.5% versus 7.3% [n=11/151], p<0.0001, Table 3), and had significantly higher grade tumors (2.33 versus 1.98, p=0.029).

TABLE 3

Histologic breast cancer subtype and history of hormone replacement therapy use.

| | | KRAS-variant | Non-KRAS-variant | P value |
|---|---|---|---|---|
| Never on HRT | ER+ | 77.1% (27/35) | 85.2% (127/149) | NS |
| | HER2+ | 22.9% (8/28) | 19.9% (28/141) | NS |
| | TN | 11.4% (4/35) | 9.3% (14/150) | NS |
| | Grade | 2.24 | 2.16 | NS |
| On HRT when diagnosed (current) | ER+ | 85.5% (47/55) | 84.8% (156/184) | NS |
| | HER2+ | 16.3% (7/43) | 12.0% (17/142) | NS |
| | TN | 3.6% (2/56) | 6.6% (12/182) | NS |
| | Grade | 2.02 | 2.01 | NS |
| Stopped HRT before diagnosis (past) | ER+ | 53.1% (17/32) | 89.7% (139/155) | <0.0001 |
| | HER2+ | 6.9% (2/29) | 11.2% (15/134) | NS |
| | TN | 35.5% (11/31) | 7.3% (11/151) | <0.0001 |
| | Grade | 2.33 | 1.98 | p = 0.029 |

Tumor grade between all KRAS-variant versus non-KRAS-variant patients was non-significant. KRAS-variant patients were significantly more likely to have triple negative breast cancers as a group (p=0.029). KRAS-variant patients with a history of past HRT use were significantly more likely to have TNBC than never or current HRT users with the KRAS-variant. KRAS-variant past HRT users were significantly more likely to have higher grade and TNBC than non-variant past users. There were no differences in cancer subtype by HRT use for non-variant patients.

KRAS-Variant BC Patients Versus Controls

We then evaluated if differences in hormonal exposures might impact BC risk in women with the KRAS-variant, by comparing hormonal exposures in KRAS-variant BC patients (n=286) with a cohort of KRAS-variant cancer free unaffected controls (n=80). In univariate analysis we found numerous significant differences, including factors associated with HRT use, pregnancy, OCP use and BMI (Table 4). By multivariate analysis we confirmed that KRAS-variant BC patients remained significantly more likely to have a lower BMI, and have fewer live births than KRAS-variant cancer free controls (Table 5). Of note, we found no difference in age of diagnosis vs age of enrollment between the BC patients and the controls.

TABLE 4

KRAS-variant breast cancer patients (cases) versus unaffected KRAS-variant controls.

| | | Control | Case | | |
|---|---|---|---|---|---|
| | | N | | | |
| | | 80 | 286 | | |
| Age at menopause | (Range/years) | 50 (32-58) | 48 (27-57) | 0.037 | Mann Whitney U |
| HRT use (post-menopausal at dx/sampling only) | Yes | 18 (43%) | 104 (73%) | <0.001 | $X^2$ |
| | No | 24 (57%) | 39 (27%) | | |
| | Median duration of HRT (post-menopausal at dx) | 84 (6-360) | 60 (1-444) | 0.769 | Mann Whitney U |
| Pregnancy | Nulliparous | 10 (12.5%) | 62 (22%) | 0.064 | $X^2$ |
| | ≥1 pregnancy | 70 (87.5%) | 222 (78%) | | |
| | Number of pregnancies* | 3 (1-7) | 2 (1-9) | 0.194 | Mann Whitney U |
| | Number of live births* | 3 (0-7) | 2 (0-5) | <0.001 | Mann Whitney U |
| | Median age at first birth | 24 (16-38) | 26 (16-39) | 0.009 | Mann Whitney U |

TABLE 4-continued

| KRAS-variant breast cancer patients (cases) versus unaffected KRAS-variant controls. | | | | |
|---|---|---|---|---|
| | | Control | Case | |
| | | N | | |
| | | 80 | 286 | |
| OCP | Yes | 63 (79%) | 251 (88%) | 0.041 $X^2$ |
| | No | 17 (21%) | 35 (12%) | |
| | Duration (years) | 5 (0.5-28) | 7.5 (0.1-40) | 0.182 Mann Whitney U |
| BMI | | 29 (17.6-75.3) | 24 (18.0-47.0) | <0.001 Mann Whitney U |

*Excluding nulliparous women

Women with breast cancer with the KRAS-variant have several significant differences in hormonal exposures when compared to cancer free KRAS-variant women.

TABLE 5

KRAS-variant BC cases compared to KRAS-variant controls. Age at diagnosis/enrollment

| Age at diagnosis | Odds Ratio (95% CI) | p-value |
|---|---|---|
| Use of HRT1 | 0.95 (0.89-1.03) | 0.211 |
| Duration of HRT use | 2.73 (0.91-8.18) | 0.07 |
| Number of live births | 1.00 (0.99-1.00) | 0.62 |
| Age at first birth | 0.62 (0.39-0.98) | 0.04 |
| BMI | 1.11 (0.99-1.24) | 0.06 |
| OCP use2 | 0.93 (0.87-1.00) | 0.04 |
| Duration of OCP | 2.15 (0.63-7.42) | 0.22 |
| Oophorectomy before | 1.01 (0.94-1.09) | 0.77 |
| diagnosis/enrollment3 | | |
| | 1.3 (0.44-3.89) | 0.63 |

1Compared to no HRT use.
2Compared to no OCP use.
3Compared to no ovarian procedure.

Women with breast cancer with the KRAS-variant by a binary logistic model were significantly more likely to have fewer live births, and to have a lower Body Mass Index (BMI)

Estrogen Withdrawal and Transformation in KRAS-Variant MCF10A Cell Lines

Figure 1B:
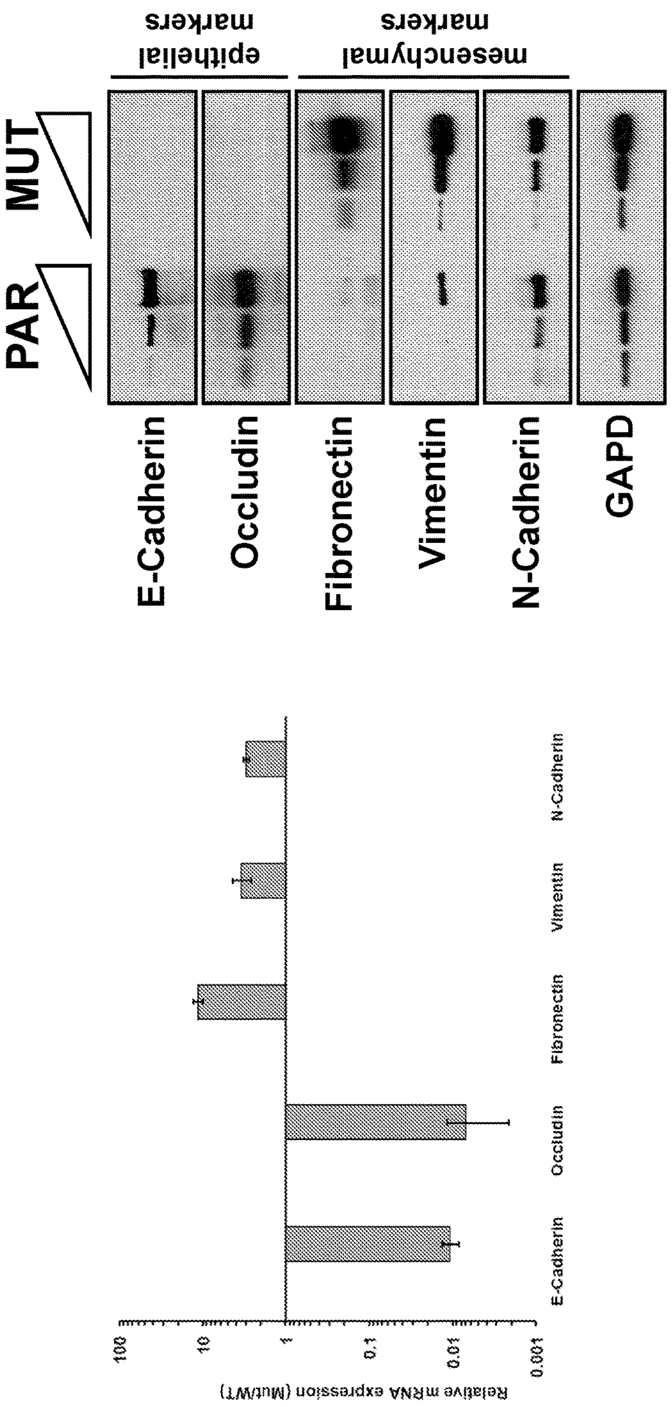
FIG. 1B shows a panel of epithelial and mesenchymal markers measured by mRNA and Western Analysis. Levels of epithelial and mesenchymal markers were consistent with KRAS-variant lines having undergone an epithelial to mesenchymal transition (EMT) and being more mesenchymal, with significantly lower E-Cadherin and Occludin, and significantly higher Fibronectin and Vimentin than the non-variant line.
Figure 1C:
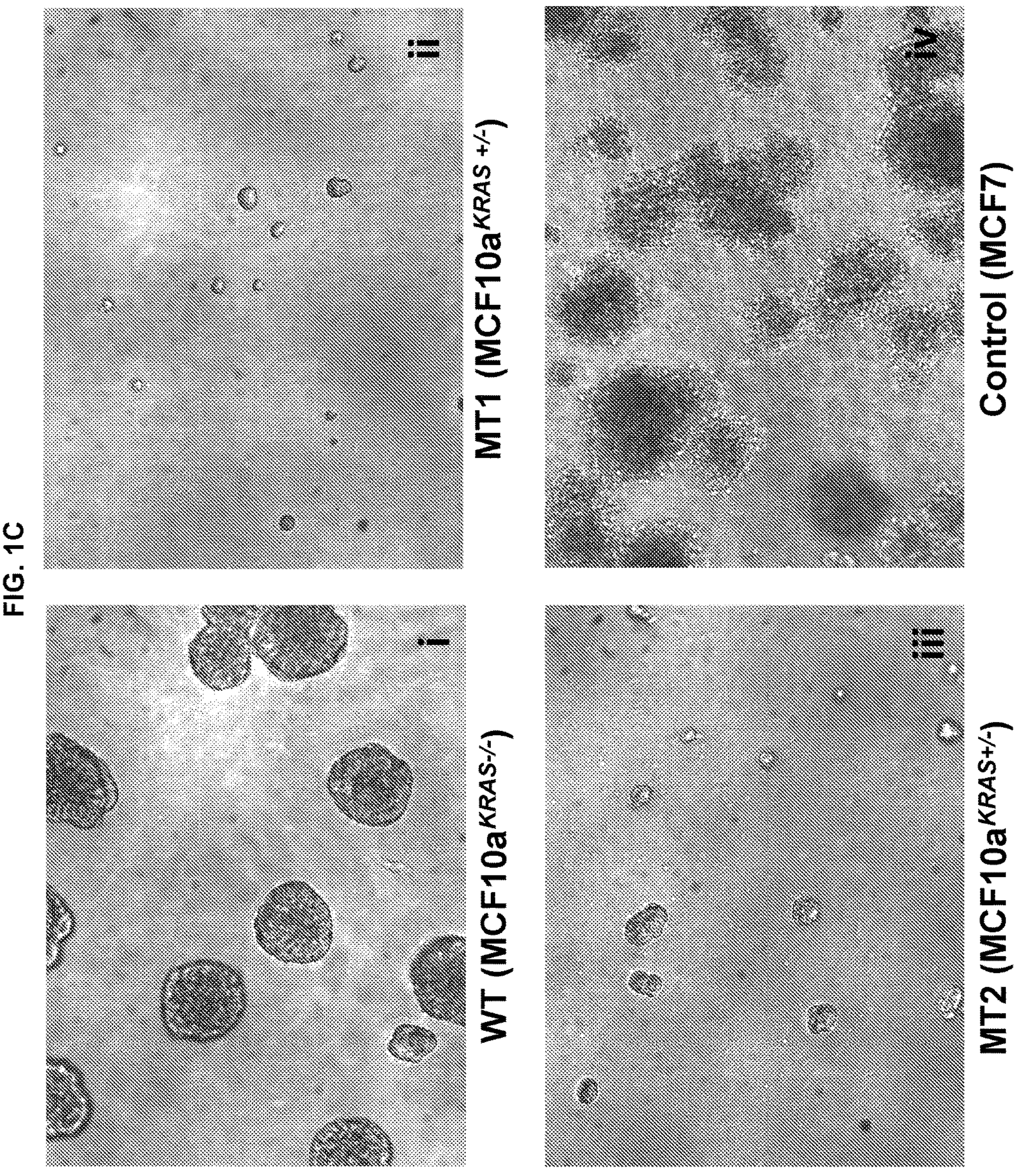
FIG. 1C shows that KRAS-variant cell lines (MUT1 and MUT2) were unable to form normal acini in 3D culture, unlike the non-variant (PAR) line or control MCF7 line.
Figure 1D:
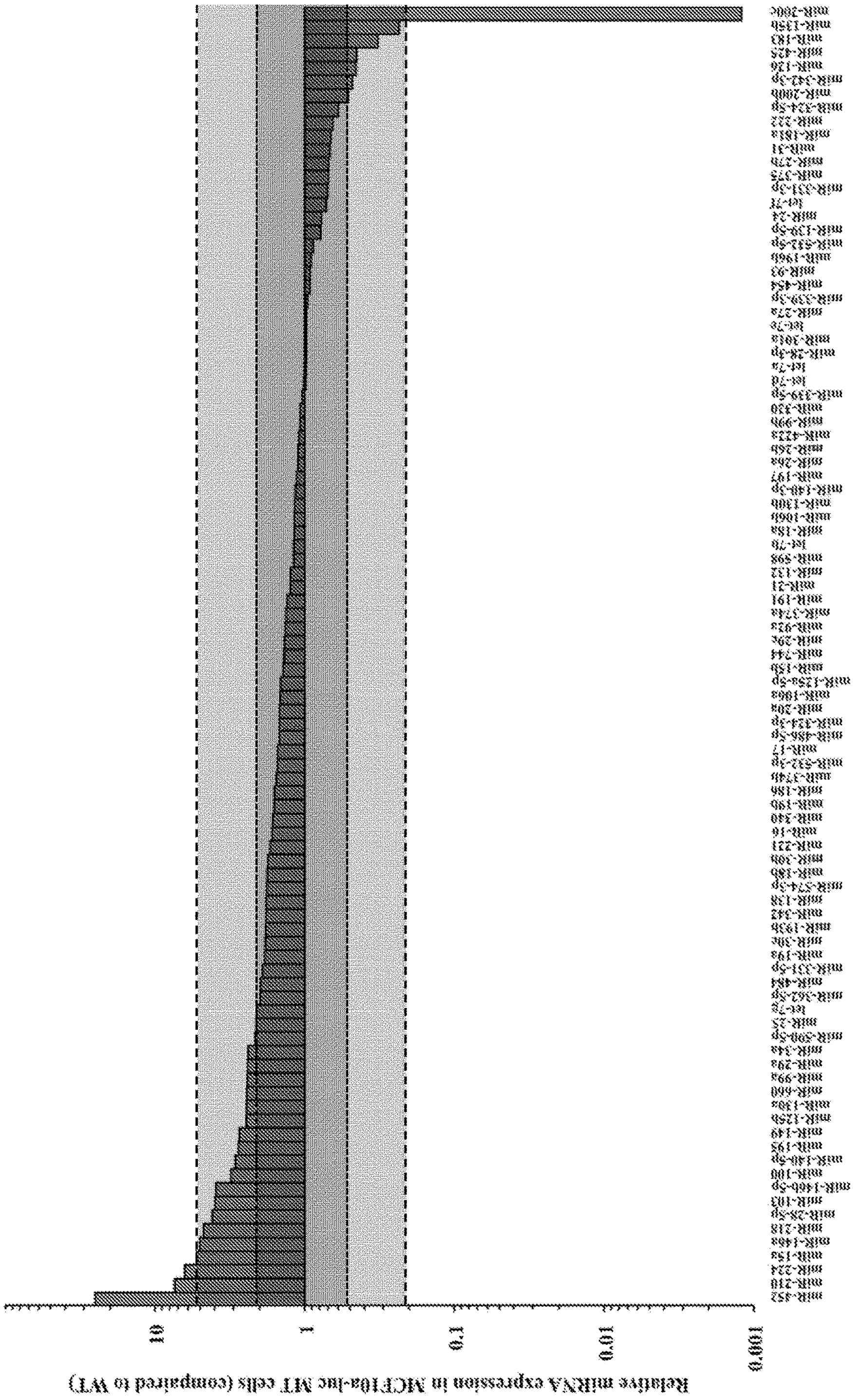
FIG. 1D shows that miRNA expression was significantly different between KRAS-variant cells (MUT) and the non-variant (PAR) cells. As shown, miR-200c was the most dramatically down-regulated miR in the MUT cells.
Figure 2:
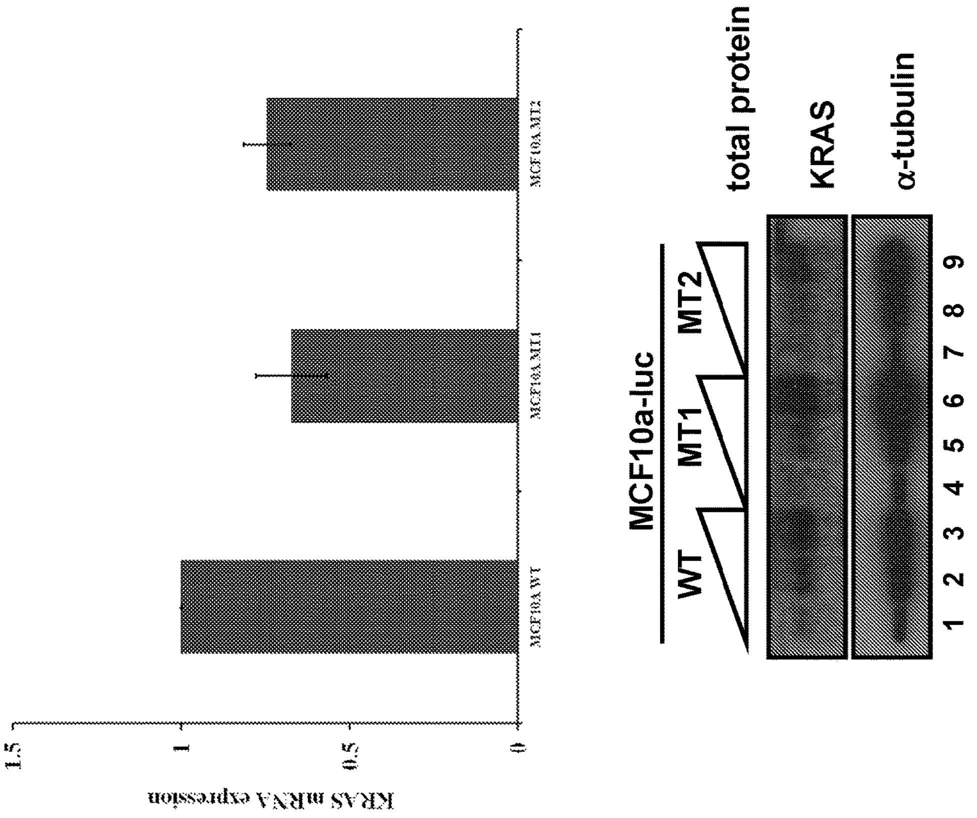
FIG. 2 shows a bar graph and Western Blot depicting that KRAS mRNA was lower in the MT cells, but KRAS protein was slightly elevated.

Based on the findings that a low estrogen state was associated with BC for women with the KRAS-variant, the hypothesis that estrogen withdrawal could lead to increased BC risk was tested. Isogenic MCF10a lines were created with (MCF10a$^{KRAS+/-}$, MT1 and MT2) versus without (MCF10a$^{KRAS-/-}$, WT) the KRAS-variant. When grown under standard conditions, MT lines exhibited a mesenchymal spindle phenotype, suggesting a baseline epithelial to mesenchymal transition (EMT) in the presence of the KRAS-variant FIG. 1A). Consistent with this altered phenotype, a panel of epithelial and mesenchymal markers measured by mRNA and Western Blot Analysis were consistent with MT lines having undergone EMT and being more mesenchymal, with significantly lower E-Cadherin and Occludin, and significantly higher Fibronectin and Vimentin than the WT line (FIG. 1B). Furthermore, in 3D culture, MT cells formed small irregular shaped spheroids, whereas WT cells formed well-organized, polarized spheroids, supporting a mesenchymal phenotype for MT lines (FIG. 1C) (Debnath, supra). Potentially explaining the EMT, miRNA expression was significantly different between the MT and WT cells, with miR-200c being most dramatically down-regulated miR in the MT cells (FIG. 1D). In addition, we found that KRAS mRNA was lower in the MT cells, but KRAS protein was slightly elevated (FIG. 2).

Figure 1E:
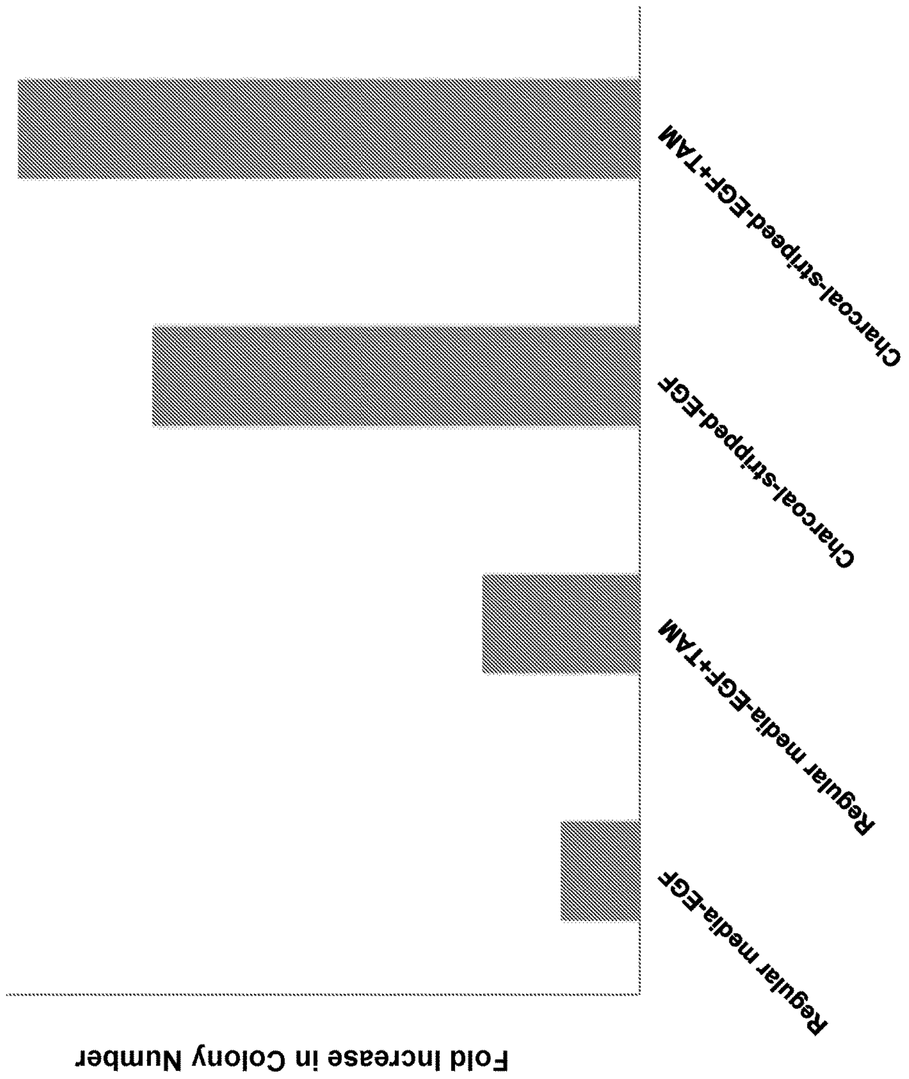
FIG. 1E shows that in KRAS-variant cell lines, removal of estrogen or estrogen activity leads to increased colony formation, which indicates transformation from a non-cancer to a cancer. KRAS-variant cell lines exhibit a 2-fold increased colony formation rate in the presence of Tamoxifen (TAM), a 6.2 fold increased colony formation rate in charcoal stripped media (media from which estrogen has been removed), and a 7.9 fold increased colony formation rate with both TAM and charcoal stripped media.
Figure 3:
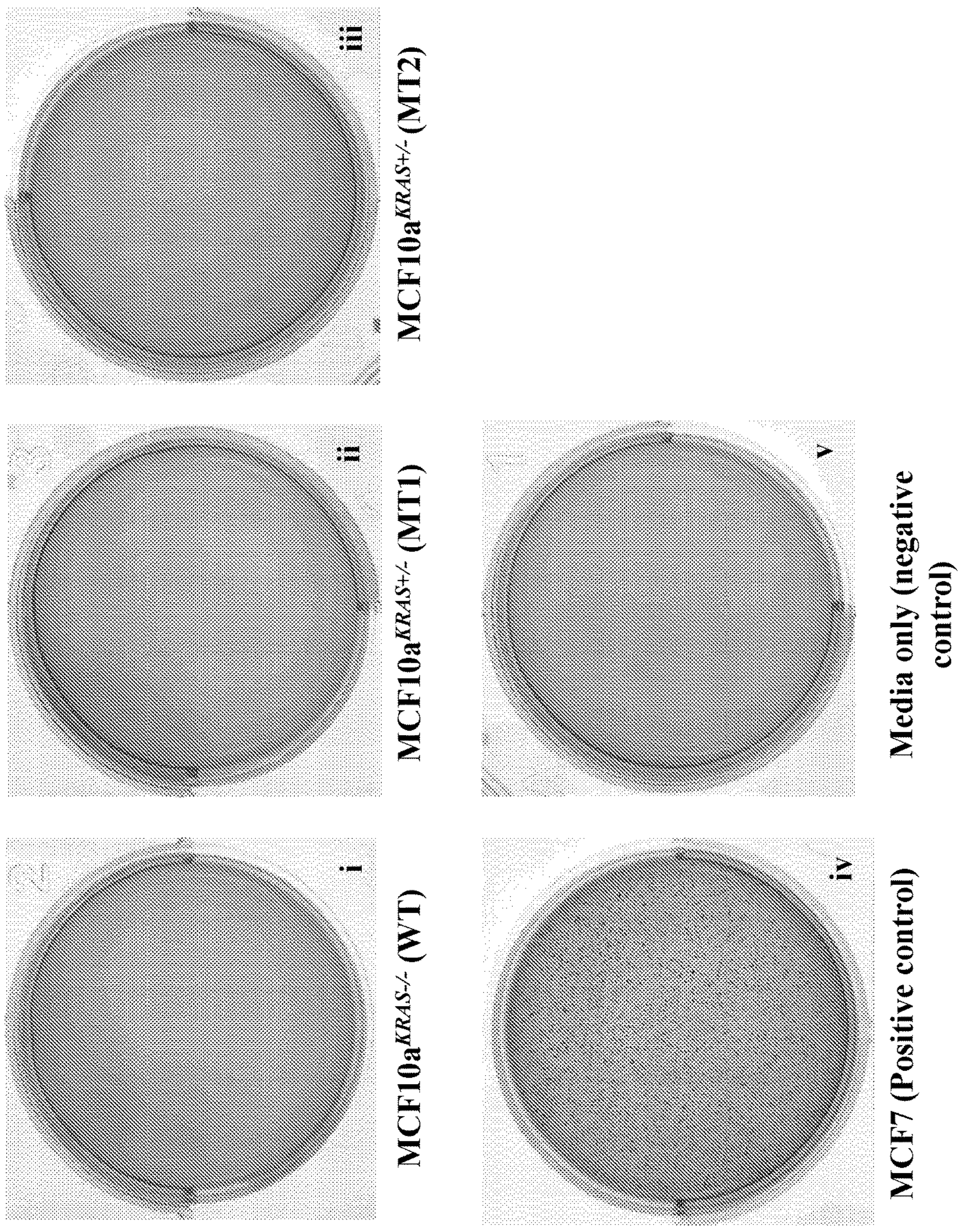
FIG. 3 shows representative images of MCF10A cells lines with (MCF10a$^{KRAS+/-}$; MT1 and MT2) versus without (MCF10a$^{KRAS-/-}$; WT) the KRAS-variant grown in soft agar. All the cell lines were seeded in soft agar of 6-tissue culture plates ($7.5\times10^4$ cells per well). The cells were grown for 21 days to allow for anchorage-independent colony formation. MCF10a WT (i) and isogenic KRAS-variant cell lines, MT1 (ii) and MT2 (iii) did not show anchorage-independent cell growth in soft agar. The MCF7 (positive control; iv) formed numerous colonies. The media only (negative control; v) did not show any colony formation.
Figure 4:
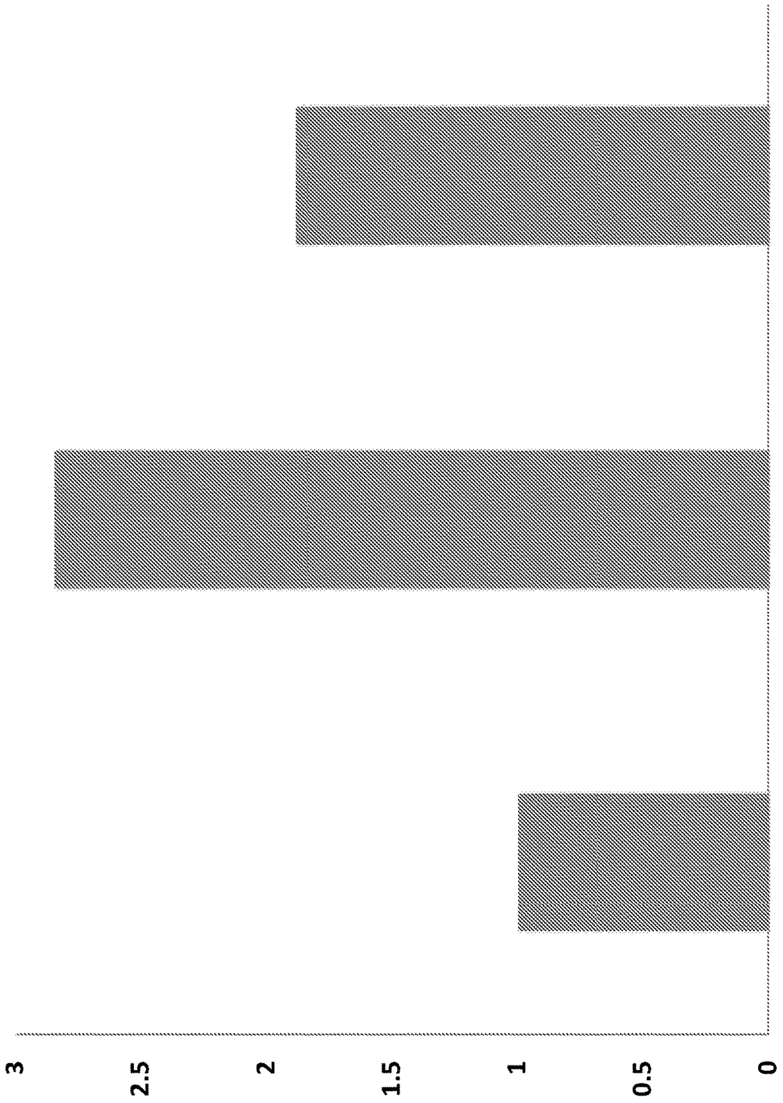
FIG. 4 shows that in KRAS-variant cell lines, returning estrogen to charcoal-stripped media resulted in decreased transformation (i.e., decreased colony formation), supporting that the increase in transformation in charcoal-stripped media was due to estrogen removal.

Next, WT and MT lines were plated in soft agar to test for transformation, as measured by anchorage independent growth. There was no colony formation seen in the presence of EGF during the course of the experiment for the WT lines or the MT lines, indicating that neither, at baseline, was transformed (FIG. 3). However, when the lines were grown without EGF, as is standard to promote transformation, the WT lines formed no colonies, while the MT lines had colony formation by the second soft agar plating, indicating a significantly enhanced tumor initiation phenotype. The impact of estrogen withdrawal on this transformation was next evaluated by the use of charcoal stripped serum, tamoxifen, or a combination of the two. In both MUT cell lines, a 2-fold increased colony formation rate was seen in the presence of Tamoxifen, a 6.2 fold increased colony formation rate in charcoal stripped media, and a 7.9 fold increased colony formation rate with the combination ($p<0.001$, FIG. 1E). Supporting that the impact of charcoal stripping on transformation was due to estrogen depletion, return of estrogen to the media resulted in decreased transformation for the MT cell lines ($p=0.018$, FIG. 4). These findings biologically confirm wide spread transformation in normal breast epithelium with acute estrogen withdrawal in breast cells with the KRAS-variant.

Figure 5:
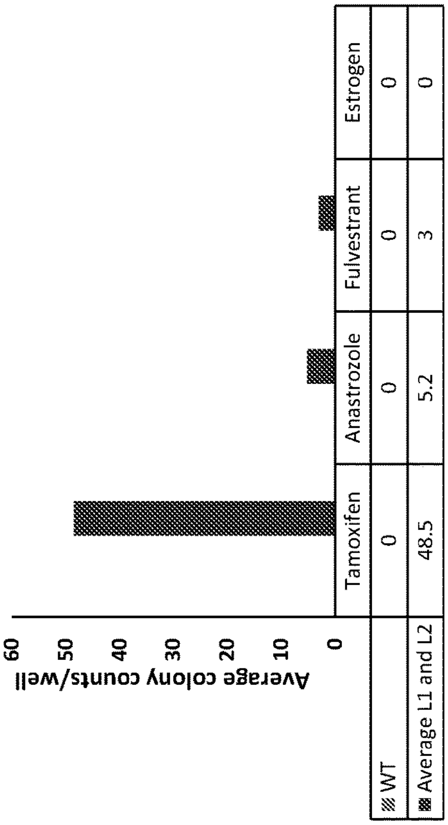
FIG. 5 shows that different anti-estrogen treatments lead to different transformation rates in anchorage independent growth assays in the KRAS-variant MCF10A lines (L1 and L2) compared to the parental (WT) MCF10A line. Estrogen treatment prevents transformation.

Next, different forms of estrogen inhibitors were tested to determine their effects on transformation in the presence of the KRAS-variant. Tamoxifen (ER antagonist in breast), anastrozole (aromatase inhibitor, inhibiting estrogen synthesis), and fulvestrant (a complete ER antagonist) were administered to parental (WT) or two KRAS-variant (L1 and L2) MCF10A cell lines and anchorage independent growth was assessed using the colony formation assay described above. Tamoxifen led to the highest level of transformation, with almost 10 times more colonies formed than the anastrozole or fulvestrant treatments. In contrast, estrogen supplementation prevented transformation (FIG. 5). These results show that certain estrogen-inhibiting agents may be more likely to transform breast epithelial cells in KRAS-variant cells, and therefore may be contraindicated for KRAS-variant BC patients.

Multiple Primary Breast Cancer Risk in KRAS-Variant BC Patients

Based on the findings that estrogen exposures before the first BC diagnosis appeared to increase BC risk for women with the KRAS-variant, and because estrogen withdrawal is often a goal of breast cancer treatment, the risk and timing of multiple primary breast cancer was evaluated in these women. Women with the KRAS-variant (GT or GG) exhibited a 2.04-fold increase in the odds of having a second primary BC, when compared to women without the variant ($p<0.001$). For the first time, the inventors of the instant application discovered a genetic dose effect of the KRAS-variant, with women heterozygous (GT) for the KRAS-variant exhibiting a 1.81-fold increase in the odds of having a second primary BC (p=0.006), and women homozygous for the KRAS-variant exhibiting an 11.64-fold increase in the odds of having second primary BC (p<0.001), compared to non-variant BC patients. (Table 6.)

Figure 6:
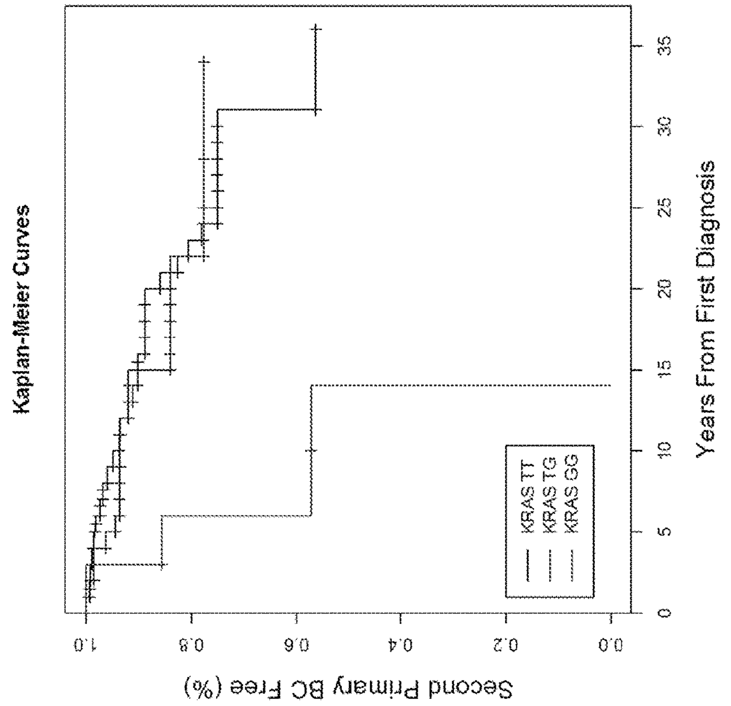
FIG. 6 shows a Kaplan-Meier curve showing that women with a KRAS GG mutation tend to be at higher risk of developing second primary tumors (HR=13.49, 95% C.I.=4.20-43.06, p. val<0.001). These data are derived from 7 patients.

Next, it was determined whether second breast cancer for KRAS-variant patients occurred at the same time as their first diagnosis (synchronous MPBC), or if they continued to be at an elevated risk of a second breast cancer after their first diagnosis (metachronous MPBC). Women with the KRAS-variant exhibited a 2.63-fold increase in the odds of being diagnosed with a synchronous second primary BC, when compared to women without the KRAS-variant (6.79% vs. 2.70% with synchronous MPBC, p=0.001). This was again most pronounced for women homozygous for the KRAS-variant, who had a 12.03-fold increased odds of having a synchronous second primary BC compared to non-variant patients (25.02% with synchronous MPBC, p=0.003). Women with the KRAS-variant continued to be at an elevated risk for a metachronous breast cancer, with a 1.72-fold increase in the odds of developing a second primary tumor (8.05% vs 4.84% with metachronous MPBC, p=0.05) when compared to non-variant patients. This difference was primarily explained by the large increase in the odds of metachronous BC for the homozygous KRAS-variant group, who exhibited a 14.72-fold increase in the odds of developing a second primary BC after their first BC diagnosis (p<0.001). (Table 6, FIG. 6).

Women with the KRAS-variant are significantly more likely to develop a synchronous or metachronous second primary breast cancer, especially homozygous (GG) patients.

MPBC risk for KRAS-variant patients was evaluated, controlling for extent of surgery and time of follow up. KRAS-variant and non-variant patients did not significantly differ in their choice of lumpectomy, unilateral mastectomy or bilateral mastectomy at the time of diagnosis. (Table 7A & 7B). Controlling for extent of primary surgery, women with the KRAS-variant who had a unilateral mastectomy were significantly more likely to have a synchronous second primary tumor (OR=18.42, CI=3.88-87.82, p<0.001) in the breast when compared to non-variant unilateral mastectomy patients. In addition, controlling for number of years at risk, women with the KRAS-variant treated with a lumpectomy were significantly more likely to develop a second, metachronous primary breast cancer (OR=1.84, CI-1.03-3.27, p=0.04) when compared to non-variant patients treated in the same manner (Table 8).

TABLE 6

Second breast cancer risk in KRAS-variant breast cancer patients.

Second Primary Tumor Risk

| KRAS-Variant Genotype | No. | % Second Primary BC (95% C.I.) | OR (95% C.I.) [p. val] |
|---|---|---|---|
| TT | 1357 | 6.78% (5.56%-8.25%) | 1.00 (Baseline) |
| TG or GG | 286 | 12.93% (9.52%-17.32%) | 2.04 (1.36-3.06) [<0.001] |
| TG | 275 | 11.64% (8.35%-15.99%) | 1.81 (1.18-2.77) [0.006] |
| GG | 11 | 45.39% (20.25%-73.04%) | 11.44 (3.42-37.87) [<0.001] |

Synchronous Second Primary Tumors

| KRAS Variants | No. | % Second Primary BC (95% C.I.) {OR} [p. val] Combined | Unilateral | Contralateral |
|---|---|---|---|---|
| TT | 1561 | 2.70% (1.95%-3.73%) {1.00-baseline} | 0.23% (0.07%-0.72%) {1.00-baseline} | 2.62% (1.87%-3.64%) {1.00-baseline} |
| TG or GG | 1296 | 6.79% (4.31%-10.50%) {2.63} [0.001] | 4.49% (2.58%-7.71%) {20.29} [<0.001] | 3.00% (1.51%-5.90%) {1.15} [0.73] |
| TG | 257 | 6.23% (3.85%-9.87%) {2.39} [0.005] | 3.85% (2.09%-6.98%) {17.22} [<0.001] | 3.09% (1.55%-6.04%) {1.19} [0.67] |
| GG | 8 | 25.02% (6.27%-62.24%) {12.03} [0.003] | 30.03% (10.05%-62.01%) {184} [<0.001] | 10.02% (1.39%-46.57%) {4.15} [0.18] |

Metachronous Second Primary Tumors (Excluding double mastectomy cases)

| KRAS Variants | No. | % Second Primary BC (95% C.I.) OR [p. val] Combined | Unilateral | Contralateral |
|---|---|---|---|---|
| TT | 1393 | 4.84% (3.74%-6.23%) {1.00-baseline} | 0.52% (0.23%-1.14%) {1.00-baseline} | 4.40% (3.36%-5.76% {1.00-baseline} |
| TG or GG | 236 | 8.05% (5.19%-12.33%) {1.72} [0.04] | 2.10% (0.88%-4.97%) {4.12} [0.02] | |
| TG | 229 | 6.98% (4.32%-11.09%) {1.48} [0.16] | 1.73% (0.65%-4.52%) {3.38} [0.06] | 6.73% (4.16%-10.73%) {1.57} [0.13] |
| GG | 7 | 42.80% (14.32%-76.88%) {14.72} [<0.001] | 22.23% (5.57%-57.88%) {54.8} [<0.001] | |

TABLE 7A

| Frequencies of unilateral and bilateral mastectomy by KRAS variant | | | |
|---|---|---|---|
| KRAS Variant | No. | % Unilateral (95% C.I.) OR [p. val] | % Bilateral (95% C.I.) OR [p. val] |
| TT | 1352 | 22.86% (20.70%, 25.16%) {1.00-baseline} | 14.13% (12.37%, 16.09%) {1.00-baseline} |
| TG or GG | 284 | 23.60% (19.03%, 28.89%) {1.04} [0.78] | 13.02% (9.59%, 17.45%) {0.91} [0.63] |

The association of lobular histology with the KRAS-variant and second BC risk was evaluated, and it was found that the KRAS-variant was not associated with lobular histology, although in agreement with prior reports, lobular histology was associated with increased rates of second primary BC, both synchronous and metachronous (Table 9A & 9B). Controlling for lobular histology, extent of surgery and number of years at risk, women with the KRAS-variant who had a unilateral mastectomy were significantly more likely to have a synchronous second primary tumor (OR=40.75, CI=4.98-339.72, p<0.01). In addition, women with the KRAS-variant treated with lumpectomy and with

TABLE 7B

Frequencies of second primary BC by Extent of surgery

Combined Synchronous and Metachronous second Primary Tumors

| Surgery | No. | % Second Primary BC (95% C.I.) | OR (95% C.I.) [p. val] |
|---|---|---|---|
| Lumpectomy | 1081 | 6.66% (5.32%, 8.31%) | 1.00 - Baseline |
| Unilateral | 327 | 5.50% (3.49%, 8.57%) | 0.82 (0.48, 1.38) [0.45] |
| Bilateral | 228 | 16.66% (12.36%, 22.06%) | 2.80 (1.84, 4.27) [<0.001] |

Synchronous Second Primary Tumors

| | | % Second Primary BC (95% C.I.) {OR} [p. val] | | |
|---|---|---|---|---|
| Surgery | No. | Combined | Unilateral | Contralateral |
| Lumpectomy | 1016 | 0.79% (0.39%, 1.565) {1.00-baseline} | 0.20% (0.05%, 0.78%) {1.00-baseline} | 0.69% (0.33%, 1.44%) {1.00-baseline} |
| Unilateral | 318 | 3.13% (1.68%, 5.69%) {4.08} [0.003] | 3.13% (1.69%, 5.685) {16.38} [<0.001] | 0.31% (0.04%, 2.16%) {0.45} [0.45] |
| Bilateral | 228 | 16.59% (12.34%, 21.955) {25.11} [<0.001] | 1.75% (0.65%, 4.57%) {9.03} [0.01] | 15.29% (11.16%, 20.57%) {26.04} [<0.001] |

Metachronous Second Primary Tumors (Excluding double mastectomy cases)

| Surgery | No. | % Second Primary BC (95% C.I.) | OR (95% C.I. ) [p. val] |
|---|---|---|---|
| Lumpectomy | 1074 | 6.05% (4.78%, 7.65%) | 1.00 - Baseline |
| Unilateral | 318 | 2.84% (1.48%, 5.35%) | 0.45 (0.22, 0.92) [0.03] |

TABLE 8

| | No. | KRAS TT % Second Primary BC (95% C.I.) | KRAS TG/GG OR (95% C.I.) [p. val] |
|---|---|---|---|
| Synchronous Second Primary Tumors | | | |
| Lumpectomy | 1016 | 0.58% (0.24%, 1.39%) | 4.32 (1.15, 16.40) [0.03] |
| Unilateral | 318 | 0.79% (0.20%, 3.12%) | 18.42 (3.88, 87.82) [<0.001] |
| Bilateral | 228 | 16.13% (11.59%, 22.05%) | 1.34 (0.56, 3.20) [0.45] |
| Metachronous Second Primary Tumors (Adjusted by no. of years at risk) | | | |
| Lumpectomy | 1074 | 5.18% (3.89%, 6.86%) | 1.84 (1.03, 3.27) [0.04] |
| Unilateral | 318 | 2.52% (1.20%, 5.25%) | 2.18 (0.62, 7.72) [0.23] |

Time to Second Primary Tumor Recurrence

| | No. | KRAS TT Hazard Ratio (95% C.I.) [p. val] | KRAS Hazard Ratio (95% C.I.) [p. val] TG/GG |
|---|---|---|---|
| Lumpectomy | 1074 | 1.00 - baseline | 1.74 (0.99, 3.07) [0.05] |
| Unilateral | 318 | 0.56 (0.18, 0.97) [0.04] | 1.43 (0.36, 5.74) [0.61] |

Odds Ratios (OR) and Hazard Ratios (HR) refer to a comparison of KRAS variants within extent of surgery category non-lobular histology continued to be significantly more likely to develop a second, metachronous primary breast cancer (OR=2.01, CI=1.05-3.86, p=0.04). Similar conclusions were found using a time to event analysis (HR=2.01, p=0.03) (Table 10).

To confirm that having the KRAS-variant was an independent predictor of MPBC, we performed a multivariate analysis using a logistic regression model, assuming that the predictors included in the model had a linear additive structure. We confirmed using this model that the KRAS-variant was an independent predictor of MPBC risk considering all other risk factors (OR=2.26, CI 1.44-2.26, P<0.001, Table 11).

TABLE 9A

| Combined Synchronous and Metachronous second Primary Tumors | | | |
|---|---|---|---|
| KRAS Variant | No. | % Lobular (95% C.I.) | OR (95% C.I.) [p. val] |
| TT | 1183 | 15.30% (13.36%, 17.46%) | 1.00 (Baseline) |
| TG or GG | 249 | 12.45% (8.89%, 17.13%) | 0.79 (0.52, 1.18) [0.25] |
| TG | 239 | 12.55% (8.92%, 17.41%) | 0.79 (0.52, 1.20) [0.28] |
| GG | 10 | 9.96% (1.39%, 46.46%) | 0.61 (0.08, 4.83) [0.65] |

TABLE 9B

| Frequencies of second primary BC by Lobular Status | | | |
|---|---|---|---|
| | No. | % Second Primary BC (95% C.I.) | OR (95% C.I.) [p. val] |
| Combined Synchronous and Metachronous second Primary Tumors | | | |
| Non Lobular | 1220 | 7.79% (6.41%, 9.42%) | 1.00 (Baseline) |
| Lobular | 212 | 13.68% (9.67%, 18.99%) | 1.88 (1.20, 2.93) [0.006] |
| Synchronous Second Primary Tumors | | | |
| Non Lobular | 1663 | 3.27% (2.39%, 4.46%) | 1.00 (Baseline) |
| Lobular | 196 | 6.63% (3.89%, 11.10%) | 2.10 (1.10, 4.03) [0.02] |
| Metachronous Second Primary Tumors (Excluding double mastectomy cases) | | | |
| Non Lobular | 1041 | 5.48% (4.25%, 7.03%) | 1.00 (Baseline) |
| Lobular | 156 | 10.27% (6.39%, 16.12%) | 1.97 (1.10, 3.54) [0.02] |

TABLE 10

Second breast cancer risk in KRAS-variant breast cancer patients controlling for lobular histology, extent of surgery and time.
Frequencies of second primary BC by Extent of Surgery, Histology and Time

| | | No. | KRAS TT % Second Primary BC (95% C.I.) | KRAS TG/GG OR (95% C.I.) [p. val] |
|---|---|---|---|---|
| Synchronous Tumors | | | | |
| Lumpectomy | Non-Lobular | 748 | 0.51% (0.19%-1.36%) | 4.43 (0.97-20.38) [>0.5] |
| | Lobular | 97 | 0.94% (0.29%-2.95%) | 2.88 (0.40-20.99) [>0.5] |
| Unilateral | Non-Lobular | 247 | 0.38% (0.05%-2.67%) | 40.75 (4.98-339.72) [<0.01] |
| | Lobular | 45 | 0.70% (0.09%-5.20%) | 26.55 (2.42-295.05) [<0.01] |
| Bilateral | Non-Lobular | 166 | 13.62% (8.96%-20.15%) | 6.44 (0.98-41.97) [>0.5] |
| | Lobular | 54 | 22.57% (12.93%-36.29%) | 0.95 (0.24-3.75) [>0.5] |
| Metachronous Second Primary Tumors (Adjusted by no. years at risk) | | | | |
| Lumpectomy | Non-Lobular | 792 | 4.89% (3.49%-6.80%) | 2.01 (1.05-3.86) [0.04] |
| | Lobular | 110 | 12.08% (7.23%-19.46%) | 1.08 (0.21-5.38) [>0.5] |
| Unilateral | Non-Lobular | 245 | 1.77% (0.76%-4.06%) | 1.54 (0.29-8.27) [>0.5] |
| | Lobular | 47 | 4.59% (1.86%-10.82%) | 0.83 (0.10-6.92) [>0.5] |

TABLE 10-continued

Second breast cancer risk in KRAS-variant breast cancer patients controlling for lobular histology, extent of surgery and time.
Frequencies of second primary BC by Extent of Surgery, Histology and Time

| Time to Second Primary Tumor Recurrence | | | | |
|---|---|---|---|---|
| | | No. | KRAS TT HR (95% C.I.) [p. val] | KRAS TG/GG HR (95% C.I.) [p. val] |
| Lumpectomy | Non-Lobular | 792 | 1.00-Baseline | 2.01 (1.08-3.77) [0.03] |
| | Lobular | 110 | 2.39 (1.31-4.36) [<0.001] | 1.38 (0.30-6.21) [>0.5] |
| Unilateral | Non-Lobular | 245 | 0.34 (0.15-0.81) [<0.001] | 1.31 (0.26-6.69) [>0.5] |
| | Lobular | 47 | 0.82 (0.30-2.29) [>0.5] | 0.89 (0.11-7.23) [>0.5] |

Odds Ratios (OR) and Hazard Rations (HR) refer to a comparison of KRAS-variants within extent of surgery category and lobular status Women with the KRAS-variant continue to be at a significantly increased risk of synchronous and metachronous breast cancer when controlling for lobular histology, extent of surgery and time.

TABLE 11

The KRAS-variant is an independent predictor of multiple primary breast cancer in a multivariable model.
Multivariable analysis of multiple cancer risk

| | OR (95% C.I.) [p. val] |
|---|---|
| Baseline | Prob = 8.78% |
| KRAS | 2.26 (2.26, 1.44) [<0.001] |
| Mastectomy (Unilateral) | 0.56 (0.56, 0.30) [0.071] |
| Mastectomy (Bilateral) | 2.54 (2.54, 1.58) [<0.001] |
| Lobular | 1.64 (1.64, 0.99) [0.054] |
| ER positive | 0.87 (0.87, 0.50) [0.623] |
| Ovaries removed | 1.30 (1.30, 0.84) [0.243] |
| BMI | 1.00 (1.00, 0.96) [0.947] |
| BCP | 1.10 (1.10, 0.60) [0.758] |
| Personal Cancer History | 1.29 (1.29, 0.78) [0.322] |
| Age at Diagnosis | 1.04 (1.04, 1.01) [0.010] |
| Menopause at Diagnosis | 0.40 (0.40, 0.22) [0.003] |
| Ever pregnant | 0.91 (0.91, 0.56) [0.698] |

Results are based on a logistic regression model, and predictors are included in the model assuming a linear additive structure.

The results described herein indicate that estrogen withdrawal increases BC risk in women with the KRAS-variant, who are also significantly more likely to present with and develop MPBC. This finding was confirmed biologically in cell lines with the KRAS variant compared to isogenic controls. Accordingly, the present invention provides methods for identifying subject with a KRAS-variant and for preventing cancer by administering to the KRAS-variant subject an amount of estrogen effective to reduce the risk of developing cancer, and for treating cancer by gradually decreasing estrogen exposure in a KRAS-variant subject to reduce the risk of aggressive tumor growth.

The results described herein also indicate that BC risk for women with the KRAS-variant appears to be increased when they are in a low estrogen state, and that abrupt estrogen withdrawal, as found with oophorectomy, discontinuation of HRT, or in the cell line assays described herein, enhances transformation and can increase their risk of aggressive tumor biology. In addition, women with the KRAS-variant are significantly more likely to have multiple primary synchronous BC, although also continue to be at risk of metachronous BC development. Further, homozygous KRAS-variant mutant patients are at significantly higher risk than heterozygotes.

The role of estrogen withdrawal on BC risk for women with the KRAS-variant could be due to a relationship between the KRAS-variant, its downstream pathways and estrogen signaling, as there are known interactions between estrogen signaling and the RAS pathway. Alternatively, the relationship between estrogen and the KRAS-variant may instead be due to alterations in miRNA expression or regulation caused by this powerful hormone. In support of the later, we have previously shown that TNBC tumors from women with the KRAS-variant have significantly higher aromatase expression and ER Beta expression. Both of these genes are regulated by the miRNA let-7, which is known to be low in KRAS-variant associated tissues and tumors. One could speculate that sudden estrogen withdrawal disrupts these biological interactions in KRAS-variant tissues, ultimately leading to escape, independent signaling and growth, and oncogenesis. Regardless, our cell line findings confirm that breast cells with the KRAS-variant are transformed by estrogen withdrawal. In addition, our clinical findings that BC patients with the KRAS-variant are more likely to have an oophorectomy than non-variant patients, have a lower BMI, and thus lower circulating estrogen than controls, and that HRT discontinuation leads to aggressive tumor biology, supports the hypothesis that acute estrogen withdrawal alters breast cell biology for KRAS-variant individuals.

A genetic marker of increased risk of synchronous multiple primary breast cancer has not been previously identified. Other breast cancer associated genetic mutations are generally considered to predict an increased risk of second metachronous breast cancers, likely due to the continued DNA damage-prone state of the tissues in these individuals. Women with the KRAS-variant are at highest risk of presenting with synchronous multiple primary cancers, suggesting perhaps that there was an initiating “event” that promoted cancer initiation, and that their tissues were globally impacted. Their increased risk of metachronous BC may be due to treatment for their first breast cancer, as BC treatments general involve estrogen withdrawal.

The findings described herein further highlight the critical importance of studying 3'UTR miRNA binding site mutations in the appropriate context. Simply put, 3'UTR mutations should be viewed as an entirely different paradigm of cancer causing mutation. Instead of being a mutation that impacts appropriate DNA repair, like BRCA mutations, they are mutations that alter the appropriate cellular response to external factors. Therefore, the general strategy to increase patient numbers by combining patients of numerous ethnic backgrounds and cultures is clearly a poor solution when studying such 3'UTR mutations. As these large consortia have begun to study these mutations, it should not be ignored that their findings may be biased against mutations that are perhaps the most important—mutations that might be altered, or controlled, by lifestyle modifications. Utilizing the appropriate cohorts to define the factors that can modify cancer risk in meaningful 3'UTR mutations should be an extremely high priority in cancer prevention studies at this time.

Limitations of the studies described herein include self-reported lifestyle factors for our BC patients, which are prone to recall bias. However, our findings regarding the impact of estrogen withdrawal on KRAS-variant tissues were biologically confirmed in cell lines, further validating our results. In addition, some of the strongest findings, regarding tumor biology post-HRT, and second breast cancer risk, were all confirmed with pathology documentation. Another limitation of the study is that the population was not prospectively collected, allowing survivor bias for metachronous BC development. However, the cohorts in this study have identical length of follow up, and we controlled for time in our metachronous breast cancer analysis. Also, as KRAS-variant women are significantly more likely to be diagnosed with premenopausal TNBC, which is the most deadly form of breast cancer, if anything, this bias should have decreased the ability to show such associations for women with the KRAS-variant.

While prospective studies are ongoing, women with the KRAS-variant appear to clearly be significantly at risk for multiple primary breast cancer. Those at highest risk are women shown to be homozygous for the KRAS-variant, a genotype occurring in ~3% of the population, significantly more frequent than BRCA mutations (~0.25%).

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the entire contents of each individual publication or patent document was incorporated herein.

What is claimed is:

1. A method for preventing breast cancer in a KRAS-variant subject in need thereof, the method comprising:

administering to the KRAS-variant subject an amount of estrogen effective to reduce the risk of developing breast cancer.

2. The method of claim 1, wherein about 0.01 mg to about 0.1 mg estrogen is administered per day.

3. The method of claim 1, the method comprising administering HRT to an oophorectomy patient to compensate for the sudden loss in estrogen that occurs with ovary removal, and gradually decreasing the HRT dose over time.

4. The method of claim 1, wherein the method further comprises detecting a single nucleotide polymorphism (SNP) at position 4 of the let-7 complementary site 6 of KRAS in a patient sample wherein the presence of said SNP indicates an increased risk of developing cancer in said subject.

* * * * *

SEQUENCE LISTING

```
<160> NUMBER OF SEQ ID NOS: 17

<210> SEQ ID NO 1
<211> LENGTH: 25
<212> TYPE: RNA
<213> ORGANISM: Homo sapiens
<220> FEATURE:
<223> OTHER INFORMATION: See specification as filed for detailed
      description of substitutions and preferred embodiments

<400> SEQUENCE: 1

gacaguggaa guuuuuuuuu ccucg                                           25


<210> SEQ ID NO 2
<211> LENGTH: 19
<212> TYPE: RNA
<213> ORGANISM: Homo sapiens
<220> FEATURE:
<223> OTHER INFORMATION: See specification as filed for detailed
      description of substitutions and preferred embodiments

<400> SEQUENCE: 2

auuaguguca ucuugccuc                                                  19


<210> SEQ ID NO 3
<211> LENGTH: 25
<212> TYPE: RNA
<213> ORGANISM: Homo sapiens
<220> FEATURE:
<223> OTHER INFORMATION: See specification as filed for detailed
      description of substitutions and preferred embodiments

<400> SEQUENCE: 3

aaugcccuac aucuuauuuu ccuca                                           25


<210> SEQ ID NO 4
<211> LENGTH: 24
```

<212> TYPE: RNA
<213> ORGANISM: Homo sapiens
<220> FEATURE:
<223> OTHER INFORMATION: See specification as filed for detailed description of substitutions and preferred embodiments

<400> SEQUENCE: 4
gguucaagcg auucucgugc cucg 24

<210> SEQ ID NO 5
<211> LENGTH: 24
<212> TYPE: RNA
<213> ORGANISM: Homo sapiens
<220> FEATURE:
<223> OTHER INFORMATION: See specification as filed for detailed description of substitutions and preferred embodiments

<400> SEQUENCE: 5
ggcugguccg aacuccugac cuca 24

<210> SEQ ID NO 6
<211> LENGTH: 21
<212> TYPE: RNA
<213> ORGANISM: Homo sapiens
<220> FEATURE:
<223> OTHER INFORMATION: See specification as filed for detailed description of substitutions and preferred embodiments

<400> SEQUENCE: 6
gauucaccca ccuuggccuc a 21

<210> SEQ ID NO 7
<211> LENGTH: 28
<212> TYPE: RNA
<213> ORGANISM: Homo sapiens
<220> FEATURE:
<223> OTHER INFORMATION: See specification as filed for detailed description of substitutions and preferred embodiments

<400> SEQUENCE: 7
ggguguuaag acuugacaca guaccucg 28

<210> SEQ ID NO 8
<211> LENGTH: 28
<212> TYPE: RNA
<213> ORGANISM: Homo sapiens
<220> FEATURE:
<223> OTHER INFORMATION: See specification as filed for detailed description of substitutions and preferred embodiments

<400> SEQUENCE: 8
agugcuuaug aggggauauu uaggccuc 28

<210> SEQ ID NO 9
<211> LENGTH: 5436
<212> TYPE: DNA
<213> ORGANISM: Homo sapiens

<400> SEQUENCE: 9
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gagagtggag gatgcttttt atacattggt 660
gagggagatc cgacaataca gattgaaaaa aatcagcaaa gaagaaaaga ctcctggctg 720
tgtgaaaatt aaaaaatgca ttataatgta atctgggtgt tgatgatgcc ttctatacat 780
tagttcgaga aattcgaaaa cataaagaaa agatgagcaa agatggtaaa aagaagaaaa 840
agaagtcaaa gacaaagtgt gtaattatgt aaatacaatt tgtacttttt tcttaaggca 900
tactagtaca agtggtaatt tttgtacatt acactaaatt attagcattt gttttagcat 960
tacctaattt ttttcctgct ccatgcagac tgttagcttt taccttaaat gcttatttta 1020
aaatgacagt ggaagttttt ttttcctcta agtgccagta ttcccagagt tttggttttt 1080
gaactagcaa tgcctgtgaa aaagaaactg aatacctaag atttctgtct tggggttttt 1140
ggtgcatgca gttgattact tcttattttt cttaccaatt gtgaatgttg gtgtgaaaca 1200
aattaatgaa gcttttgaat catccctatt ctgtgtttta tctagtcaca taaatggatt 1260
aattactaat ttcagttgag accttctaat tggtttttac tgaaacattg agggaacaca 1320
aatttatggg cttcctgatg atgattcttc taggcatcat gtcctatagt ttgtcatccc 1380
tgatgaatgt aaagttacac tgttcacaaa ggttttgtct cctttccact gctattagtc 1440
atggtcactc tccccaaaat attatatttt ttctataaaa agaaaaaaat ggaaaaaaat 1500
tacaaggcaa tggaaactat tataaggcca tttccttttc acattagata aattactata 1560
aagactccta atagcttttc ctgttaaggc agacccagta tgaaatgggg attattatag 1620
caaccatttt ggggctatat ttacatgcta ctaaattttt ataataattg aaaagatttt 1680
aacaagtata aaaaattctc ataggaatta aatgtagtct ccctgtgtca gactgctctt 1740
tcatagtata actttaaatc ttttcttcaa cttgagtctt tgaagatagt tttaattctg 1800
cttgtgacat taaaagatta tttgggccag ttatagctta ttaggtgttg aagagaccaa 1860
ggttgcaagg ccaggccctg tgtgaacctt tgagctttca tagagagttt cacagcatgg 1920
actgtgtccc cacggtcatc cagtgttgtc atgcattggt tagtcaaaat ggggagggac 1980
tagggcagtt tggatagctc aacaagatac aatctcactc tgtggtggtc ctgctgacaa 2040
atcaagagca ttgcttttgt ttcttaagaa aacaaactct tttttaaaaa ttacttttaa 2100
atattaactc aaaagttgag attttggggt ggtggtgtgc caagacatta attttttttt 2160
taaacaatga agtgaaaaag ttttacaatc tctaggtttg gctagttctc ttaacactgg 2220
ttaaattaac attgcataaa cacttttcaa gtctgatcca tatttaataa tgctttaaaa 2280
taaaaataaa aacaatcctt ttgataaatt taaaatgtta cttattttaa aataaatgaa 2340
gtgagatggc atggtgaggt gaaagtatca ctggactagg aagaaggtga cttaggttct 2400
agataggtgt cttttaggac tctgattttg aggacatcac ttactatcca tttcttcatg 2460
ttaaaagaag tcatctcaaa ctcttagttt ttttttttta caactatgta atttatattc 2520
catttacata aggatacact tatttgtcaa gctcagcaca atctgtaaat ttttaaccta 2580
tgttacacca tcttcagtgc cagtcttggg caaaattgtg caagaggtga agtttatatt 2640

-continued

```
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
aaggtgtatg tcagatattc atattgaccc aaatgtgtaa tattccagtt ttctctgcat   3840
aagtaattaa aatatactta aaaattaata gttttatctg ggtacaaata aacaggtgcc   3900
tgaactagtt cacagacaag gaaacttcta tgtaaaaatc actatgattt ctgaattgct   3960
atgtgaaact acagatcttt ggaacactgt ttaggtaggg tgttaagact tacacagtac   4020
ctcgtttcta cacagagaaa gaaatggcca tacttcagga actgcagtgc ttatgagggg   4080
atatttaggc ctcttgaatt tttgatgtag atgggcattt ttttaaggta gtggttaatt   4140
acctttatgt gaactttgaa tggtttaaca aaagatttgt ttttgtagag attttaaagg   4200
gggagaattc tagaaataaa tgttacctaa ttattacagc cttaaagaca aaaatccttg   4260
ttgaagtttt ttttaaaaaaa gctaaattac atagacttag gcattaacat gtttgtggaa   4320
gaatatagca gacgtatatt gtatcatttg agtgaatgtt cccaagtagg cattctaggc   4380
tctatttaac tgagtcacac tgcataggaa tttagaacct aacttttata ggttatcaaa   4440
actgttgtca ccattgcaca attttgtcct aatatataca tagaaacttt gtggggcatg   4500
ttaagttaca gtttgcacaa gttcatctca tttgtattcc attgattttt tttttcttct   4560
aaacattttt tcttcaaaca gtatataact ttttttaggg gatttttttt tagacagcaa   4620
aaactatctg aagatttcca tttgtcaaaa agtaatgatt tcttgataat tgtgtagtaa   4680
tgttttttag aacccagcag ttaccttaaa gctgaattta tatttagtaa cttctgtgtt   4740
aatactggat agcatgaatt ctgcattgag aaactgaata gctgtcataa aatgaaactt   4800
tctttctaaa gaaagatact cacatgagtt cttgaagaat agtcataact agattaagat   4860
ctgtgtttta gtttaatagt ttgaagtgcc tgtttgggat aatgataggt aatttagatg   4920
aatttagggg aaaaaaaagt tatctgcaga tatgttgagg gcccatctct ccccccacac   4980
ccccacagag ctaactgggt tacagtgttt tatccgaaag tttccaattc cactgtcttg   5040
```

tgttttcatg ttgaaaatac ttttgcattt ttcctttgag tgccaatttc ttactagtac 5100
tatttcttaa tgtaacatgt ttacctggaa tgtattttaa ctatttttgt atagtgtaaa 5160
ctgaaacatg cacattttgt acattgtgct ttcttttgtg ggacatatgc agtgtgatcc 5220
agttgttttc catcatttgg ttgcgctgac ctaggaatgt tggtcatatc aaacattaaa 5280
aatgaccact cttttaattg aaattaactt ttaaatgttt ataggagtat gtgctgtgaa 5340
gtgatctaaa atttgtaata tttttgtcat gaactgtact actcctaatt attgtaatgt 5400
aataaaaata gttacagtga caaaaaaaaa aaaaaa 5436

<210> SEQ ID NO 10
<211> LENGTH: 5312
<212> TYPE: DNA
<213> ORGANISM: Homo sapiens

<400> SEQUENCE: 10
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gggtgttgat gatgccttct atacattagt 660
tcgagaaatt cgaaaacata aagaaaagat gagcaaagat ggtaaaaaga agaaaaagaa 720
gtcaaagaca aagtgtgtaa ttatgtaaat acaatttgta ctttttttctt aaggcatact 780 agtacaagtg gtaatttttg tacattacac taaattatta gcatttgttt tagcattacc 840
taattttttt cctgctccat gcagactgtt agcttttacc ttaaatgctt attttaaaat 900
gacagtggaa gttttttttt cctctaagtg ccagtattcc cagagttttg gtttttgaac 960
tagcaatgcc tgtgaaaaag aaactgaata cctaagattt ctgtcttggg gtttttggtg 1020
catgcagttg attacttctt atttttctta ccaattgtga atgttggtgt gaaacaaatt 1080
aatgaagctt ttgaatcatc cctattctgt gttttatcta gtcacataaa tggattaatt 1140
actaatttca gttgagacct tctaattggt ttttactgaa acattgaggg aacacaaatt 1200
tatgggcttc ctgatgatga ttcttctagg catcatgtcc tatagtttgt catccctgat 1260
gaatgtaaag ttacactgtt cacaaaggtt ttgtctcctt tccactgcta ttagtcatgg 1320
tcactctccc caaaatatta tatttttttct ataaaaagaa aaaaatggaa aaaaattaca 1380
aggcaatgga aactattata aggccatttc cttttcacat tagataaatt actataaaga 1440
ctcctaatag cttttcctgt taaggcagac ccagtatgaa atggggatta ttatagcaac 1500
cattttgggg ctatatttac atgctactaa atttttataa taattgaaaa gattttaaca 1560
agtataaaaa attctcatag gaattaaatg tagtctccct gtgtcagact gctctttcat 1620
agtataactt taaatctttt cttcaacttg agtctttgaa gatagtttta attctgcttg 1680

-continued

```
tgacattaaa agattatttg ggccagttat agcttattag gtgttgaaga gaccaaggtt   1740
gcaaggccag gccctgtgtg aacctttgag ctttcataga gagtttcaca gcatggactg   1800
tgtccccacg gtcatccagt gttgtcatgc attggttagt caaaatgggg agggactagg   1860
gcagtttgga tagctcaaca agatacaatc tcactctgtg gtggtcctgc tgacaaatca   1920
agagcattgc ttttgtttct taagaaaaca aactcttttt taaaaattac ttttaaatat   1980
taactcaaaa gttgagattt tggggtggtg gtgtgccaag acattaattt tttttttaaa   2040
caatgaagtg aaaaagtttt acaatctcta ggtttggcta gttctcttaa cactggttaa   2100
attaacattg cataaacact tttcaagtct gatccatatt taataatgct ttaaaataaa   2160
aataaaaaca atccttttga taaatttaaa atgttactta ttttaaaata aatgaagtga   2220
gatggcatgg tgaggtgaaa gtatcactgg actaggaaga aggtgactta ggttctagat   2280
aggtgtcttt taggactctg attttgagga catcacttac tatccatttc ttcatgttaa   2340
aagaagtcat ctcaaactct tagttttttt tttttacaac tatgtaattt atattccatt   2400
tacataagga tacacttatt tgtcaagctc agcacaatct gtaaattttt aacctatgtt   2460
acaccatctt cagtgccagt cttgggcaaa attgtgcaag aggtgaagtt tatatttgaa   2520
tatccattct cgttttagga ctcttcttcc atattagtgt catcttgcct ccctaccttc   2580
cacatgcccc atgacttgat gcagttttaa tacttgtaat tcccctaacc ataagattta   2640
ctgctgctgt ggatatctcc atgaagtttt cccactgagt cacatcagaa atgccctaca   2700
tcttatttcc tcagggctca agagaatctg acagatacca taaagggatt tgacctaatc   2760
actaatttc aggtggtggc tgatgctttg aacatctctt tgctgcccaa tccattagcg    2820
acagtaggat ttttcaaacc tggtatgaat agacagaacc ctatccagtg gaaggagaat   2880
ttaataaaga tagtgctgaa agaattcctt aggtaatcta taactaggac tactcctggt   2940
aacagtaata cattccattg ttttagtaac cagaaatctt catgcaatga aaaatacttt   3000
aattcatgaa gcttactttt tttttttggt gtcagagtct cgctcttgtc acccaggctg   3060
gaatgcagtg gcgccatctc agctcactgc aacctccatc tcccaggttc aagcgattct   3120
cgtgcctcgg cctcctgagt agctgggatt acaggcgtgt gccactacac tcaactaatt   3180
tttgtatttt taggagagac ggggtttcac cctgttggcc aggctggtct cgaactcctg   3240
acctcaagtg attcacccac cttggcctca taaacctgtt ttgcagaact catttattca   3300
gcaaatattt attgagtgcc taccagatgc cagtcaccgc acaaggcact gggtatatgg   3360
tatccccaaa caagagacat aatcccggtc cttaggtagt gctagtgtgg tctgtaatat   3420
cttactaagg cctttggtat acgacccaga gataacacga tgcgtatttt agttttgcaa   3480
agaaggggtt tggtctctgt gccagctcta taattgtttt gctacgattc cactgaaact   3540
cttcgatcaa gctactttat gtaaatcact tcattgtttt aaaggaataa acttgattat   3600
attgtttttt tatttggcat aactgtgatt cttttaggac aattactgta cacattaagg   3660
tgtatgtcag atattcatat tgacccaaat gtgtaatatt ccagttttct ctgcataagt   3720
aattaaaata tacttaaaaa ttaatagttt tatctgggta caaataaaca ggtgcctgaa   3780
ctagttcaca gacaaggaaa cttctatgta aaaatcacta tgatttctga attgctatgt   3840
gaaactacag atctttggaa cactgtttag gtagggtgtt aagacttaca cagtacctcg   3900
tttctacaca gagaaagaaa tggccatact tcaggaactg cagtgcttat gaggggatat   3960
ttaggcctct tgaatttttg atgtagatgg gcattttttt aaggtagtgg ttaattacct   4020
ttatgtgaac tttgaatggt ttaacaaaag atttgttttt gtagagattt taaaggggga   4080
```

gaattctaga aataaatgtt acctaattat tacagcctta aagacaaaaa tccttgttga 4140
agttttttta aaaaaagcta aattacatag acttaggcat taacatgttt gtggaagaat 4200
atagcagacg tatattgtat catttgagtg aatgttccca agtaggcatt ctaggctcta 4260
tttaactgag tcacactgca taggaattta gaacctaact tttataggtt atcaaaactg 4320
ttgtcaccat tgcacaattt tgtcctaata tatacataga aactttgtgg ggcatgttaa 4380
gttacagttt gcacaagttc atctcatttg tattccattg attttttttt tcttctaaac 4440
atttttcttt caaacagtat ataacttttt ttaggggatt tttttttaga cagcaaaaac 4500
tatctgaaga tttccatttg tcaaaaagta atgatttctt gataattgtg tagtaatgtt 4560
ttttagaacc cagcagttac cttaaagctg aatttatatt tagtaacttc tgtgttaata 4620
ctggatagca tgaattctgc attgagaaac tgaatagctg tcataaaatg aaactttctt 4680
tctaaagaaa gatactcaca tgagttcttg aagaatagtc ataactagat taagatctgt 4740
gttttagttt aatagtttga agtgcctgtt tgggataatg ataggtaatt tagatgaatt 4800
taggggaaaa aaaagttatc tgcagatatg ttgagggccc atctctcccc ccacaccccc 4860
acagagctaa ctgggttaca gtgttttatc cgaaagtttc caattccact gtcttgtgtt 4920
ttcatgttga aaatactttt gcatttttcc tttgagtgcc aatttcttac tagtactatt 4980
tcttaatgta acatgtttac ctggaatgta ttttaactat ttttgtatag tgtaaactga 5040
aacatgcaca ttttgtacat tgtgctttct tttgtgggac atatgcagtg tgatccagtt 5100
gttttccatc atttggttgc gctgacctag gaatgttggt catatcaaac attaaaaatg 5160
accactcttt taattgaaat taacttttaa atgtttatag gagtatgtgc tgtgaagtga 5220
tctaaaattt gtaatatttt tgtcatgaac tgtactactc ctaattattg taatgtaata 5280
aaaatagtta cagtgacaaa aaaaaaaaaa aa 5312

<210> SEQ ID NO 11
<211> LENGTH: 5436
<212> TYPE: DNA
<213> ORGANISM: Homo sapiens

<400> SEQUENCE: 11
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gagagtggag gatgcttttt atacattggt 660
gagggagatc cgacaataca gattgaaaaa aatcagcaaa gaagaaaaga ctcctggctg 720
tgtgaaaatt aaaaaatgca ttataatgta atctgggtgt tgatgatgcc ttctatacat 780
tagttcgaga aattcgaaaa cataaagaaa agatgagcaa agatggtaaa aagaagaaaa 840

-continued

```
agaagtcaaa gacaaagtgt gtaattatgt aaatacaatt tgtacttttt tcttaaggca    900
tactagtaca agtggtaatt tttgtacatt acactaaatt attagcattt gttttagcat    960
tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aatacctaag atttctgtct tggggttttt   1140
ggtgcatgca gttgattact tcttattttt cttaccaatt gtgaatgttg gtgtgaaaca   1200
aattaatgaa gcttttgaat catccctatt ctgtgtttta tctagtcaca taaatggatt   1260
aattactaat ttcagttgag accttctaat tggtttttac tgaaacattg agggaacaca   1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaaagatta tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag attttggggt ggtggtgtgc caagacatta attttttttt   2160
taaacaatga agtgaaaaag ttttacaatc tctaggtttg gctagttctc ttaacactgg   2220
ttaaattaac attgcataaa cacttttcaa gtctgatcca tatttaataa tgctttaaaa   2280
taaaaataaa aacaatcctt ttgataaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
```

ttctcgtgcc tcggcctcct gagtagctgg gattacaggc gtgtgccact acactcaact 3300
aatttttgta tttttaggag agacggggtt tcaccctgtt ggccaggctg gtctcgaact 3360
cctgacctca agtgatgcac ccaccttggc ctcataaacc tgttttgcag aactcattta 3420
ttcagcaaat atttattgag tgcctaccag atgccagtca ccgcacaagg cactgggtat 3480
atggtatccc caaacaagag acataatccc ggtccttagg tagtgctagt gtggtctgta 3540
atatcttact aaggcctttg gtatacgacc cagagataac acgatgcgta ttttagtttt 3600
gcaaagaagg ggtttggtct ctgtgccagc tctataattg ttttgctacg attccactga 3660
aactcttcga tcaagctact ttatgtaaat cacttcattg ttttaaagga ataaacttga 3720
ttatattgtt tttttatttg gcataactgt gattctttta ggacaattac tgtacacatt 3780
aaggtgtatg tcagatattc atattgaccc aaatgtgtaa tattccagtt ttctctgcat 3840
aagtaattaa aatatactta aaaattaata gttttatctg ggtacaaata aacaggtgcc 3900
tgaactagtt cacagacaag gaaacttcta tgtaaaaatc actatgattt ctgaattgct 3960
atgtgaaact acagatcttt ggaacactgt ttaggtaggg tgttaagact tacacagtac 4020
ctcgtttcta cacagagaaa gaaatggcca tacttcagga actgcagtgc ttatgagggg 4080
atatttaggc ctcttgaatt tttgatgtag atgggcattt ttttaaggta gtggttaatt 4140
acctttatgt gaactttgaa tggtttaaca aaagatttgt ttttgtagag attttaaagg 4200
gggagaattc tagaaataaa tgttacctaa ttattacagc cttaaagaca aaaatccttg 4260
ttgaagtttt tttaaaaaaa gctaaattac atagacttag gcattaacat gtttgtggaa 4320
gaatatagca gacgtatatt gtatcatttg agtgaatgtt cccaagtagg cattctaggc 4380
tctatttaac tgagtcacac tgcataggaa tttagaacct aacttttata ggttatcaaa 4440
actgttgtca ccattgcaca attttgtcct aatatataca tagaaacttt gtggggcatg 4500
ttaagttaca gtttgcacaa gttcatctca tttgtattcc attgattttt tttttcttct 4560
aaacattttt tcttcaaaca gtatataact ttttttaggg gatttttttt tagacagcaa 4620
aaactatctg aagatttcca tttgtcaaaa agtaatgatt tcttgataat tgtgtagtaa 4680
tgttttttag aacccagcag ttaccttaaa gctgaattta tatttagtaa cttctgtgtt 4740
aatactggat agcatgaatt ctgcattgag aaactgaata gctgtcataa aatgaaactt 4800
tctttctaaa gaaagatact cacatgagtt cttgaagaat agtcataact agattaagat 4860
ctgtgtttta gtttaatagt ttgaagtgcc tgtttgggat aatgataggt aatttagatg 4920
aatttagggg aaaaaaaagt tatctgcaga tatgttgagg gcccatctct ccccccacac 4980
ccccacagag ctaactgggt tacagtgttt tatccgaaag tttccaattc cactgtcttg 5040
tgttttcatg ttgaaaatac ttttgcattt ttcctttgag tgccaatttc ttactagtac 5100
tatttcttaa tgtaacatgt ttacctggaa tgtattttaa ctatttttgt atagtgtaaa 5160
ctgaaacatg cacattttgt acattgtgct ttcttttgtg ggacatatgc agtgtgatcc 5220
agttgttttc catcatttgg ttgcgctgac ctaggaatgt tggtcatatc aaacattaaa 5280
aatgaccact cttttaattg aaattaactt ttaaatgttt ataggagtat gtgctgtgaa 5340
gtgatctaaa atttgtaata tttttgtcat gaactgtact actcctaatt attgtaatgt 5400
aataaaaata gttacagtga caaaaaaaaa aaaaaa 5436

<210> SEQ ID NO 12
<211> LENGTH: 5312
<212> TYPE: DNA

-continued

<213> ORGANISM: Homo sapiens

<400> SEQUENCE: 12
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gggtgttgat gatgccttct atacattagt 660
tcgagaaatt cgaaaacata aagaaaagat gagcaaagat ggtaaaaaga agaaaaagaa 720
gtcaaagaca aagtgtgtaa ttatgtaaat acaatttgta ctttttttctt aaggcatact 780 agtacaagtg gtaatttttg tacattacac taaattatta gcatttgttt tagcattacc 840
taattttttt cctgctccat gcagactgtt agcttttacc ttaaatgctt attttaaaat 900
gacagtggaa gttttttttt cctctaagtg ccagtattcc cagagttttg gtttttgaac 960
tagcaatgcc tgtgaaaaag aaactgaata cctaagattt ctgtcttggg gtttttggtg 1020
catgcagttg attacttctt atttttctta ccaattgtga atgttggtgt gaaacaaatt 1080
aatgaagctt ttgaatcatc cctattctgt gttttatcta gtcacataaa tggattaatt 1140
actaatttca gttgagacct tctaattggt ttttactgaa acattgaggg aacacaaatt 1200
tatgggcttc ctgatgatga ttcttctagg catcatgtcc tatagtttgt catccctgat 1260
gaatgtaaag ttacactgtt cacaaaggtt ttgtctcctt tccactgcta ttagtcatgg 1320
tcactctccc caaaatatta tatttttttct ataaaaagaa aaaaatggaa aaaaattaca 1380
aggcaatgga aactattata aggccatttc cttttcacat tagataaatt actataaaga 1440
ctcctaatag cttttcctgt taaggcagac ccagtatgaa atggggatta ttatagcaac 1500
cattttgggg ctatatttac atgctactaa atttttataa taattgaaaa gattttaaca 1560
agtataaaaa attctcatag gaattaaatg tagtctccct gtgtcagact gctctttcat 1620
agtataactt taaatctttt cttcaacttg agtctttgaa gatagtttta attctgcttg 1680
tgacattaaa agattatttg ggccagttat agcttattag gtgttgaaga gaccaaggtt 1740
gcaaggccag gccctgtgtg aacctttgag ctttcataga gagtttcaca gcatggactg 1800
tgtccccacg gtcatccagt gttgtcatgc attggttagt caaaatgggg agggactagg 1860
gcagtttgga tagctcaaca agatacaatc tcactctgtg gtggtcctgc tgacaaatca 1920
agagcattgc ttttgtttct taagaaaaca aactcttttt taaaaattac ttttaaatat 1980
taactcaaaa gttgagattt tggggtggtg gtgtgccaag acattaattt tttttttaaa 2040
caatgaagtg aaaaagtttt acaatctcta ggtttggcta gttctcttaa cactggttaa 2100
attaacattg cataaacact tttcaagtct gatccatatt taataatgct ttaaaataaa 2160
aataaaaaca atccttttga taaatttaaa atgttactta ttttaaaata aatgaagtga 2220
gatggcatgg tgaggtgaaa gtatcactgg actaggaaga aggtgactta ggttctagat 2280

-continued

```
aggtgtcttt taggactctg attttgagga catcacttac tatccatttc ttcatgttaa   2340
aagaagtcat ctcaaactct tagttttttt tttttacaac tatgtaattt atattccatt   2400
tacataagga tacacttatt tgtcaagctc agcacaatct gtaaattttt aacctatgtt   2460
acaccatctt cagtgccagt cttgggcaaa attgtgcaag aggtgaagtt tatatttgaa   2520
tatccattct cgttttagga ctcttcttcc atattagtgt catcttgcct ccctaccttc   2580
cacatgcccc atgacttgat gcagttttaa tacttgtaat tcccctaacc ataagattta   2640
ctgctgctgt ggatatctcc atgaagtttt cccactgagt cacatcagaa atgccctaca   2700
tcttatttcc tcagggctca agagaatctg acagatacca taaagggatt tgacctaatc   2760
actaatttc aggtggtggc tgatgctttg aacatctctt tgctgcccaa tccattagcg   2820
acagtaggat ttttcaaacc tggtatgaat agacagaacc ctatccagtg gaaggagaat   2880
ttaataaaga tagtgctgaa agaattcctt aggtaatcta taactaggac tactcctggt   2940
aacagtaata cattccattg ttttagtaac cagaaatctt catgcaatga aaaatacttt   3000
aattcatgaa gcttactttt ttttttggt gtcagagtct cgctcttgtc acccaggctg   3060
gaatgcagtg gcgccatctc agctcactgc aacctccatc tcccaggttc aagcgattct   3120
cgtgcctcgg cctcctgagt agctgggatt acaggcgtgt gccactacac tcaactaatt   3180
tttgtatttt taggagagac ggggtttcac cctgttggcc aggctggtct cgaactcctg   3240
acctcaagtg atgcacccac cttggcctca taaacctgtt ttgcagaact catttattca   3300
gcaaatattt attgagtgcc taccagatgc cagtcaccgc acaaggcact gggtatatgg   3360
tatccccaaa caagagacat aatcccggtc cttaggtagt gctagtgtgg tctgtaatat   3420
cttactaagg cctttggtat acgacccaga gataacacga tgcgtatttt agttttgcaa   3480
agaaggggtt tggtctctgt gccagctcta taattgtttt gctacgattc cactgaaact   3540
cttcgatcaa gctactttat gtaaatcact tcattgtttt aaaggaataa acttgattat   3600
attgtttttt tatttggcat aactgtgatt cttttaggac aattactgta cacattaagg   3660
tgtatgtcag atattcatat tgacccaaat gtgtaatatt ccagttttct ctgcataagt   3720
aattaaaata tacttaaaaa ttaatagttt tatctgggta caaataaaca ggtgcctgaa   3780
ctagttcaca gacaaggaaa cttctatgta aaaatcacta tgatttctga attgctatgt   3840
gaaactacag atctttggaa cactgtttag gtagggtgtt aagacttaca cagtacctcg   3900
tttctacaca gagaaagaaa tggccatact tcaggaactg cagtgcttat gaggggatat   3960
ttaggcctct tgaattttg atgtagatgg gcattttttt aaggtagtgg ttaattacct   4020
ttatgtgaac tttgaatggt ttaacaaaag atttgttttt gtagagattt taaaggggga   4080
gaattctaga aataaatgtt acctaattat tacagcctta aagacaaaaa tccttgttga   4140
agtttttta aaaaaagcta aattacatag acttaggcat taacatgttt gtggaagaat   4200
atagcagacg tatattgtat catttgagtg aatgttccca agtaggcatt ctaggctcta   4260
tttaactgag tcacactgca taggaattta gaacctaact tttataggtt atcaaaactg   4320
ttgtcaccat tgcacaattt tgtcctaata tatacataga aactttgtgg ggcatgttaa   4380
gttacagttt gcacaagttc atctcatttg tattccattg atttttttt tcttctaaac   4440
attttttcttt caaacagtat ataacttttt ttaggggatt tttttttaga cagcaaaaac   4500
tatctgaaga tttccatttg tcaaaaagta atgatttctt gataattgtg tagtaatgtt   4560
ttttagaacc cagcagttac cttaaagctg aatttatatt tagtaacttc tgtgttaata   4620
```

-continued

```
ctggatagca tgaattctgc attgagaaac tgaatagctg tcataaaatg aaactttctt   4680

tctaaagaaa gatactcaca tgagttcttg aagaatagtc ataactagat taagatctgt   4740

gttttagttt aatagtttga agtgcctgtt tgggataatg ataggtaatt tagatgaatt   4800

taggggaaaa aaaagttatc tgcagatatg ttgagggccc atctctcccc ccacaccccc   4860

acagagctaa ctgggttaca gtgttttatc cgaaagtttc caattccact gtcttgtgtt   4920

ttcatgttga aaatactttt gcatttttcc tttgagtgcc aatttcttac tagtactatt   4980

tcttaatgta acatgtttac ctggaatgta ttttaactat ttttgtatag tgtaaactga   5040

aacatgcaca ttttgtacat tgtgctttct tttgtgggac atatgcagtg tgatccagtt   5100

gttttccatc atttggttgc gctgacctag gaatgttggt catatcaaac attaaaaatg   5160

accactcttt taattgaaat taacttttaa atgtttatag gagtatgtgc tgtgaagtga   5220

tctaaaattt gtaatatttt tgtcatgaac tgtactactc ctaattattg taatgtaata   5280

aaaatagtta cagtgacaaa aaaaaaaaaa aa                                  5312


<210> SEQ ID NO 13
<211> LENGTH: 21
<212> TYPE: RNA
<213> ORGANISM: Homo sapiens

<400> SEQUENCE: 13

gaugcaccca ccuuggccuc a                                                21


<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

aggactctga ttttgaggac atc                                              23


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

aacatgcccc acaaagtttc                                                  20


<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

aaggcatact agtacaagtg gtaattt                                          27


<210> SEQ ID NO 17
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 17

taggagtagt acagttcatg acaaaaa                                     27
```